(12) United States Patent
Millet

(10) Patent No.: US 11,202,769 B2
(45) Date of Patent: *Dec. 21, 2021

(54) KETONE BODY ESTERS OF S-BETA-HYDROXYBUTYRATE AND/OR S-1,3-BUTANEDIOL FOR MODIFYING METABOLIC FUNCTION

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/130,498

(22) Filed: Dec. 22, 2020

(65) Prior Publication Data

US 2021/0169831 A1 Jun. 10, 2021

Related U.S. Application Data

(60) Continuation-in-part of application No. 16/783,886, filed on Feb. 6, 2020, and a continuation-in-part of application No. 16/783,844, filed on Feb. 6, 2020, which is a continuation-in-part of application No. 16/409,501, filed on May 10, 2019, now Pat. No. 10,596,131, which is a continuation-in-part of application No. 16/381,202, filed on Apr. 11, 2019, now Pat. No. 10,925,843, said application No. 16/783,886 is a continuation-in-part of application No. 16/272,192, filed on Feb. 11, 2019, now Pat. No. 10,596,130, said application No. 16/409,501 is a continuation-in-part of application No. 16/272,165, filed on Feb. 11, 2019, now Pat. No. 10,596,129, which is a continuation-in-part of application No. 16/224,408, filed on Dec. 18, 2018, now Pat. No. 10,588,876, said application No. 16/272,192 is a continuation-in-part of application No. 16/224,485, filed on Dec. 18, 2018, now Pat. No. 10,596,128, which is a division of application No. 15/936,849, filed on Mar. 27, 2018, now Pat. No. 10,245,243, said application No. 16/224,408 is a division of application No. 15/936,820, filed on Mar. 27, 2018, now Pat. No. 10,245,242.

(60) Provisional application No. 62/659,564, filed on Apr. 18, 2018, provisional application No. 62/607,578, filed on Dec. 19, 2017, provisional application No. 62/590,063, filed on Nov. 22, 2017.

(51) Int. Cl.
    *A61K 31/22* (2006.01)
    *A61K 31/047* (2006.01)
    *A61K 31/19* (2006.01)
    *A61K 9/00* (2006.01)

(52) U.S. Cl.
    CPC ............ *A61K 31/22* (2013.01); *A61K 9/0053* (2013.01); *A61K 31/047* (2013.01); *A61K 31/19* (2013.01); *A23V 2200/3322* (2013.01)

(58) Field of Classification Search
    CPC ...... A61K 31/21; A61K 31/22; A61K 9/0053; A61K 31/047; A23V 2200/3322
    See application file for complete search history.

(56) References Cited

U.S. PATENT DOCUMENTS

| | | | |
|---|---|---|---|
| 2,238,149 A | 4/1941 | Aeckerle | |
| 2,976,073 A | 3/1961 | Russell et al. | |
| 4,627,808 A | 12/1986 | Hughes | |
| 4,997,976 A * | 3/1991 | Brunengraber | C07C 69/675 180/174 |
| 5,093,044 A | 3/1992 | Wretlind et al. | |
| 5,116,868 A | 5/1992 | Chen et al. | |
| 5,288,512 A * | 2/1994 | Seiden | A23D 7/00 426/549 |
| 5,292,774 A | 3/1994 | Hiraide et al. | |
| 5,654,266 A | 8/1997 | Chen et al. | |
| 5,700,670 A | 12/1997 | Yamagishi et al. | |
| 6,207,856 B1 | 3/2001 | Veech | |
| 6,316,038 B1 | 11/2001 | Veech | |
| 6,323,237 B1 | 11/2001 | Veech | |

(Continued)

FOREIGN PATENT DOCUMENTS

| | | |
|---|---|---|
| CN | 1347319 A | 5/2002 |
| EP | 2283834 A2 | 2/2011 |

(Continued)

OTHER PUBLICATIONS

A New Toy Measuring Blood Ketones. Diet Doctor, Aug. 21, 2012. Downloaded Apr. 1, 2015. http://www.dietdoctor.com/a-new-toy-measuring-blood-ketoones.

(Continued)

*Primary Examiner* — Theodore R. Howell
(74) *Attorney, Agent, or Firm* — Workman Nydegger

(57) ABSTRACT

Compositions and methods for producing elevated blood levels of ketone bodies and modifying metabolic function in a mammal. Compositions include at least one ester of S-beta-hydroxybutyrate and/or a mono- or di-ester of S-1, 3-butanediol and at least one ketone body component. The ketone body component includes beta-hydroxybutyrate, acetoacetate, or both. The beta-hydroxybutyrate is R-beta-hydroxybutyrate, S-beta-hydroxybutyrate, or both. When the ketone body component is S-beta-hydroxybutyrate, the 1,3-butanediol is R-1,3-butanediol, S-1,3-butanediol, or both. Compositions may comprise a keto stack of multiple forms of ketone bodies.

21 Claims, 5 Drawing Sheets

(56) References Cited

U.S. PATENT DOCUMENTS

| | | |
|---|---|---|
| 6,380,244 B2 | 4/2002 | Martin et al. |
| 6,613,356 B1 | 9/2003 | Vlahakos |
| 6,706,756 B1 | 3/2004 | Fitzpatrick et al. |
| 6,835,750 B1 | 12/2004 | Henderson |
| 7,351,736 B2 | 4/2008 | Veech |
| 7,807,718 B2 | 10/2010 | Hashim et al. |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 8,748,400 B2 | 6/2014 | Henderson |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,245,242 B1 | 4/2019 | Millet |
| 10,245,243 B1 | 4/2019 | Millet |
| 10,292,592 B2 | 5/2019 | Marshall et al. |
| 10,292,952 B2 | 5/2019 | Millet |
| 10,588,876 B2 | 3/2020 | Millet |
| 10,588,877 B2 | 3/2020 | Arnold |
| 10,596,128 B2 * | 3/2020 | Millet ............. A61P 3/08 |
| 10,596,129 B2 | 3/2020 | Millet |
| 10,596,130 B2 * | 3/2020 | Millet ............. A23L 33/12 |
| 10,596,131 B2 | 3/2020 | Millet |
| 10,660,958 B2 | 5/2020 | Clarke |
| 10,736,861 B2 | 8/2020 | Millet |
| 10,925,843 B2 * | 2/2021 | Millet ............. A61K 31/19 |
| 10,973,786 B2 | 4/2021 | Millet |
| 2001/0014696 A1 | 8/2001 | Veech |
| 2001/0041736 A1 | 11/2001 | Veech |
| 2002/0013339 A1 | 1/2002 | Martin et al. |
| 2003/0022937 A1 | 1/2003 | Veech |
| 2004/0266872 A1 | 12/2004 | Veech |
| 2005/0129783 A1 | 6/2005 | McCleary et al. |
| 2007/0179197 A1 | 8/2007 | Henderson |
| 2008/0058416 A1 | 3/2008 | Greenwood et al. |
| 2008/0287372 A1 | 11/2008 | Henderson |
| 2009/0253781 A1 | 10/2009 | Veech |
| 2010/0041751 A1 | 2/2010 | Henderson |
| 2010/0197758 A1 | 8/2010 | Andrews et al. |
| 2010/0298294 A1 | 11/2010 | Clarke et al. |
| 2012/0071548 A1 | 3/2012 | Veech |
| 2012/0202891 A1 | 8/2012 | Stinchcomb et al. |
| 2013/0079406 A1 | 3/2013 | Veech |
| 2013/0337116 A1 | 12/2013 | Petralia |
| 2015/0065571 A1 | 3/2015 | Clarke et al. |
| 2015/0132280 A1 | 5/2015 | Lopez et al. |
| 2016/0193173 A1 | 7/2016 | Clarke et al. |
| 2016/0256411 A1 | 9/2016 | Aung-Din |
| 2017/0020844 A1 | 1/2017 | Galinski |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1 | 10/2017 | Cavaleri |
| 2017/0296501 A1 | 10/2017 | Lowery et al. |
| 2017/0298339 A1 | 10/2017 | Hanson et al. |
| 2017/0304564 A1 | 10/2017 | Dehaan et al. |
| 2018/0021274 A1 | 1/2018 | Patrick |
| 2018/0055797 A1 | 3/2018 | Llosa et al. |
| 2018/0057846 A1 | 3/2018 | Llosa et al. |
| 2018/0195096 A1 | 7/2018 | Veech et al. |
| 2019/0099394 A1 | 4/2019 | Ari et al. |
| 2019/0167613 A1 | 6/2019 | Millet |
| 2019/0183820 A1 | 6/2019 | Millet |
| 2019/0313682 A1 | 10/2019 | Nagel |
| 2020/0078973 A1 | 3/2020 | Valeze et al. |
| 2020/0140371 A1 | 5/2020 | Verdin et al. |

FOREIGN PATENT DOCUMENTS

| | | |
|---|---|---|
| EP | 2976073 A1 | 1/2016 |
| EP | 3094321 A1 | 11/2016 |
| JP | 11-060434 A | 3/1999 |
| JP | 2002-521330 A | 7/2002 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 03/70823 A2 | 8/2003 |
| WO | 2005/107724 A1 | 11/2005 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |
| WO | 2011/101171 A1 | 8/2011 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2017/208217 A2 | 12/2017 |
| WO | 2018/089863 A1 | 5/2018 |
| WO | 2019/018683 A1 | 1/2019 |
| WO | 2019/237152 A1 | 12/2019 |

OTHER PUBLICATIONS

Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref-sr_1_9?dchild=1 &keywords-ketone+pre+workout &qid= 1597938465&sr=8-9.

Arendash et al. "Caffeine and Coffee as Therapeutics Against Alzheimer's Disease", Journal of Alzheimer's Disease 20, 2010, S117-S126.

Arnold, Instant Ketosis?, (2013), Aug. 4, 2013 (retrieved on Apr. 21, 2017), p. 1-3. Retrieved from the internet; URL: <http://patrickarnoldblog.com/instant-ketosis/. (Year: 2013).

Bastin et al., "Salt Slection and Optimisation Procedures for Pharmaceutical New Chemical Entities", American Chemical Society and The Royal Society of Chemistry, vol. 4, No. 5, 2000, pp. 427-435.

Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.

Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).

Dolson, Laura. How to Test Your Blood for Ketones. Downloaded Apr. 1, 2015. http://lowcarbdiets.about.eom/od/KetogenicDiets/a/How-to-Test-Blood-For-Ketones.htm.

Extended European Search Report issued in PCT/US2017021886 dated Oct. 17, 2019.

First Examination Report for New Zealand Patent Application No. 711433 issued by the New Zealand Intellectual Property Office dated Mar. 10, 2016.

First Office Action issued by the Chinese State Intellectual Property Office dated Nov. 4, 2016 for corresponding Chinese Patent Application No. 201480016818.0.

Hashim, Sami A., et al., "Ketone body therapy: from the ketogenic diet to the oral administration of ketone ester", Journal of Lipid Research, vol. 55, 2014.

Haywood A, Glass BD. Pharmaceutical excipients—where do we begin? Australian Prescriber. 2011; 34: 112-114.

Henderson, Samuel T. "Ketone Bodies as a Therapeutic for Alzheimer's Disease." Neurotherapeutics. Jul. 2008;5(3):470-80.

(56) References Cited

OTHER PUBLICATIONS

Holtzman et al., "Role of adenosine receptors in caffeine tolerance", J. Pharmacol. Exp. Ther., 1991 ;256(1 ):62-68.
International Search Report and Written Opinion issued in PCT/US19/48357 dated Nov. 18, 2019.
International Search Report and Written Opinion issued in PCT/US19/48364 dated Nov. 15, 2019.
International Search Report and Written Opinion issued in PCT/US20/16952 dated Apr. 22, 2020.
International Search Report and Written Opinion issued in PCT/US20/17552 dated May 4, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion received for PCT Patent Application No. PCT/US20/37289, dated Sep. 30, 2020, 8 pages.
International Search Report and Written Opinion received for PCT Patent Application No. PCT/US2020/033159, dated Aug. 12, 2020, 9 pages.
International Search Report cited in PCT/US18/62093 dated Feb. 1, 2019.
International Search Report cited in PCT/US19/27214 dated Jun. 25, 2019.
International Search Report in PCT/US18/62096 dated Feb. 11, 2019.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
Karppanen et al., J. Human Hypertension (2005), vol. 19, pp. S10-S19. (Year: 2005).
Karppanen, H, et al., "Why and how to implement sodium, potassium, calcium, and magnesium changes in food items and diets?".
Kesl, et al., "Effects of exogenous ketone supplementation on blood ketone, glucose, triglyceride, and lipoprotein Tevels in Spraque-Dawley rals". Nutrition & Metabolism (2016).
Kirsch, Jr et al. "Butanediol Induced Ketosis Increases Tolerance to Hypoxia in the Mouse." Stroke. 1980, vol. 11, No. 3, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Krotkiewski, "Value of VLCD Supplementation with Medium Chain Triglycerides", Int J Obes Relat Metab Disord, Sep. 2001, 25(9), pp. 1393-1400.
Murray, Andrew J., et al. "Novel ketone diet enhances physical and cognitive performance", The FASEB Journal, Vo. Dec. 30, 2016.
Non-Final Office Action received for U.S. Appl. No. 16/381,202, dated Aug. 11, 2020, 8 pages.
Non-Final Office Action received for U.S. Appl. No. 16/720,211, dated Oct. 28, 2020, 14 pages.
Non-Final Rejection dated Sep. 9, 2020 for U.S. Appl. No. 16/783,956.
Notice of Allowance received for U.S. Appl. No. 15/454,157, dated Feb. 26, 2019.
Notice of Allowance received for U.S. Appl. No. 16/381,202, dated Nov. 10, 2020, 8 pages.
Notice of Allowance received for U.S. Appl. No. 16/409,501, dated Jan. 14, 2020.
Notice of Allowance received for U.S. Appl. No. 15/936,849, dated Jan. 24, 2019.
Notice of Allowance received for U.S. Appl. No. 16/272,359, dated Aug. 7, 2019.
Notice of Allowance received for U.S. Appl. No. 16/224,408, dated Nov. 27, 2019.
Notice of Allowance received for U.S. Appl. No. 16/224,485, dated Nov. 27, 2019.
Nova Max Plus Glucose and Ketone Testing with One Monitor. Downloaded Apr. 1, 2015. http://www.novacares.com/nova-max-plus/.
Parker, Steve, "Ketogenic Mediterraanean Diet: Version 2.3," Nov. 23, 2010, pp. 1-3. (Year: 2010).
PCT International Search Report and Written Opinion issued by the International Searching Authority dated Jul. 15, 2014 or International Patent Application No. PCT/US2014/031237.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nim.nih.gov/compound/Acetoacetic-acid, Retrieved on Sep. 3, 2019.
Requirement for Restriction/Election received for U.S. Appl. No. 16/551,570, dated Sep. 28, 2020, 6 pages.
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. in Journal of Liquid Chromatography & Related Technologies, 33:1047-1057 (2010) (Year: 2010).
Serum Ketones Test. MedlinePlus Medical Encyclopedia. Downloaded Apr. 1, 2015. http://www.nlm.nih.gov/medlineplus/ency/article/003498.htm.
Shigeno etal. in Biosci. Biotech. Biochem., 56(2), 320-323 (1992) (Year: 1992).
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.
Veech, et al., "Ketone Bodies Mimic the Life Span Extending Properties of Caloric Restriction", IUBMB Life Feb. 8, 2017.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.
Office Action cited in U.S. Appl. No. 16/720,211 dated Oct. 28, 2020.
Vandenberghe et al. in Can. J. Physiol. Pharmacol. 95:455-458 (2017) (Published at www.nrcresearchpress.com/cjpp on Nov. 25, 2016). (Year: 2016).
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).
International Search Report and Written Opinion received for PCT Patent Application No. PCT/US21/17078, dated Apr. 23, 2021, 9 pages.
Malo, M. S. et al., Intestinal alkaline phosphatase preserves the normal homeostasis of gut microbiota, 2010, Gut, 59, 1476-1484 (Year: 2010).
Arnold, Instant Ketosis?, (2013), Aug. 4, 2013 (retrieved on Apr. 21, 2017), p. 1-3. Retrieved from the internet; URL: < http://patrickamoldblog.com/instant-ketosis/. (Year: 2013).
International Preliminary Report on Patentability received for PCT Patent Application No. PCT/US2019/048364, dated Mar. 11, 2021, 7 pages.
Robson et al. Expert Opin. Drug Saf. (2011), vol. 10, pp. 675-685 (Year: 2011).

(56) References Cited

OTHER PUBLICATIONS

Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.

Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.

Stubbs et al., "On the Metabolism of Exogenous Ketones in Humans", frontiers in Physiology, vol. 8, 2017, 13 pages.

Tsai et al., "Stereoselective effects of 3-hydroxybutyrate on glucose utilization of rat cardiomyocytes" life Sciences 78(2006) pp. 1385-1391.

\* cited by examiner

KETONE BODY ESTERS OF S-BETA-HYDROXYBUTYRATE AND/OR S-1,3-BUTANEDIOL FOR MODIFYING METABOLIC FUNCTION

CROSS-REFERENCE TO RELATED APPLICATIONS

This application is a continuation-in-part of U.S. patent application Ser. No. 16/381,202, filed Apr. 11, 2019, which claims the benefit of U.S. Prov. App. No. 62/659,564, filed Apr. 18, 2018, which are incorporated by reference in their entirety.

This application is also a continuation-in-part of U.S. patent application Ser. No. 16/783,844, filed Feb. 6, 2020, which is a continuation-in-part of U.S. patent application Ser. No. 16/409,501, filed May 10, 2019, now U.S. Pat. No. 10,596,131, which is a continuation-in-part of U.S. patent application Ser. No. 16/272,165, filed Feb. 11, 2019, now U.S. Pat. No. 10,596,129, which is a continuation-in-part of U.S. patent application Ser. No. 16/224,408, filed Dec. 18, 2018, now U.S. Pat. No. 10,588,876, which is a division of U.S. patent application Ser. No. 15/936,820, filed Mar. 27, 2018, now U.S. Pat. No. 10,245,242, which claims the benefit of U.S. Prov. App. No. 62/590,063, filed Nov. 22, 2017, which are incorporated by reference in their entirety.

This application is also a continuation-in-part of U.S. patent application Ser. No. 16/783,886, filed Feb. 6, 2020, which is a continuation-in-part of U.S. patent application Ser. No. 16/272,192, filed Feb. 11, 2019, now U.S. Pat. No. 10,596,130, which is a continuation-in-part of U.S. patent application Ser. No. 16/224,485, filed Dec. 18, 2018, now U.S. Pat. No. 10,596,128, which is a division of U.S. patent application Ser. No. 15/936,849, filed Mar. 27, 2018, now U.S. Pat. No. 10,245,243, which claims the benefit of U.S. Prov. App. No. 62/607,578, filed Dec. 19, 2017, which are incorporated by reference in their entirety.

BACKGROUND

1. Field of the Invention

The invention relates to compositions that include an ester of S-beta-hydroxybutyrate and/or a mono- and/or di-ester of a ketone body component and S-1,3-butanediol, and methods of using the same for producing elevated blood levels of ketone bodies and modifying metabolic function in a mammal.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. Between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate to sustain ketosis.

While in ketosis, the body is in ketogenesis and is essentially burning fat for its primary fuel. The body cleaves fats into fatty acids and glycerol and transforms fatty acids into acetyl CoA molecules, which are then eventually transformed through ketogenesis into the water-soluble ketone bodies beta-hydroxybutyrate ("β-hydroxybutyrate" or "beta-hydroxybutyrate"), acetoacetate, and acetone in the liver. beta-hydroxybutyrate and acetoacetate are the ketone bodies used by the body for energy while acetone is removed as a by-product of ketogenesis.

The metabolism of ketone bodies is associated with several improvements to metabolic function, such as anti-convulsant effects, enhanced metabolism by the brain, neuroprotection, muscle sparing properties, improved cognitive and physical performance, and epigenetic effects (positive or beneficial gene expressions). Science-based improvements in efficiency of cellular metabolism, managed through ketone supplementation, can have beneficial impacts on physical, cognitive health, and psychological health, and a long-term impact on health with respect to the common avoidable diseases such as obesity, cardiovascular disease, neurodegenerative diseases, diabetes, and cancer.

SUMMARY

Disclosed herein are compositions and methods for producing elevated blood levels of ketone bodies and modifying metabolic function in a mammal. In some embodiments, a composition comprises at least one mono- or di-ester of a ketone body component and 1,3-butanediol, such as at least one ester of S-beta-hydroxybutyrate and/or a mono- or di-ester of S-1,3-butanediol and at least one ketone body component. The ketone body component is selected from beta-hydroxybutyrate, acetoacetate, or both. Some embodiments include one or more ketone bodies (beta-hydroxybutyrate and/or acetoacetate) as mono- or di-esters of S-1,3-butanediol. Other embodiments include one or more esters of S-beta-hydroxybutyrate. S-beta-hydroxybutyrate and S-1,3-butanediol have conventionally been disfavored as inert at best or even toxic at worst.

However, the inventor of the present disclosure has discovered that controlled delivery of S-beta-hydroxybutyrate and/or S-1,3-butanediol is not only safe but provides several benefits. Upon administration of a mono- or di-ester, S-1,3-butanediol is cleaved from the ketone body component by hydrolysis. The free S-1,3-butanediol is converted to S-beta-hydroxybutyrate, which can modify metabolic function in its free form and/or may be converted endogenously into R-beta-hydroxybutyrate, acetoacetate, fatty acids, and/or sterols, among other benefits of 5-beta-hydroxybutyrate described herein. S-1,3-butanediol may also be endogenously converted to R-1,3-butanediol, which is then converted to R-beta-hydroxybutyrate acetoacetate, fatty acids, and/or sterols.

Although the metabolic pathway from S-1,3-butanediol to a circulating ketone body is longer than with R-1,3-butanediol, there are several circumstances where a slower and more sustained pharmacokinetic profile is desirable. This is particularly true during a ketogenic diet, where the goal is to maintain a sustained level of circulating ketone bodies in the blood for weeks or months at a time. S-1,3-butanediol can therefore be bonded with acetoacetate and/or with one or both enantiomeric forms of beta-hydroxybutyrate to tailor a pharmacokinetic profile according to particular application needs or preferences. Such esters may also be mixed with R-1,3-butanediol or esters thereof to further modify the pharmacokinetic profile.

Some embodiments may include multiple forms of ketone bodies. Exogenous ketone bodies (i.e., beta-hydroxybutyrate and acetoacetate) may be provided in three general forms: 1) salt forms, 2) ester forms, and 3) free acid forms (i.e., beta-hydroxybutyric acid and/or acetoacetic acid). Each of these forms provides certain benefits but can have undesirable side effects. Salt forms can introduce large amounts of electrolytes into the blood stream. Ester forms can have unpleasant taste. Free acid forms can be hard on the stomach.

To better optimize the benefits and mitigate the detriments of different ketone body forms, the compositions described herein may be provided as a "stacked" mixture combining at least two of these forms. Such stacked compositions can beneficially limit the occurrence and/or severity of undesirable side-effects and/or can permit administration of higher doses of exogenous ketone bodies. Stacked compositions permit delivery of substantially higher amounts of exogenous ketone bodies while reducing or minimizing detrimental effects of delivering too much of one type of exogenous ketone body.

Moreover, S-enantiomer-containing esters and stacked compositions containing such esters can provide multiple benefits in addition to providing higher and/or more sustained levels of ketone bodies in the blood, as will be discussed more fully below, which include modifying one or more metabolic pathways as compared to an otherwise similar amount provided in a single form. For example, S-enantiomer-containing esters and stacked formulations can be tailored to provide a more preferable or more optimized release profile, such as one that combines the benefits of more rapid onset with the benefits of a more extended release, and/or one that provides an overall greater pharmacokinetic area under the curve (AUC). S-enantiomer-containing esters and stacked compositions therefore provide for timed delivery or availability of ketone bodies, which provides for more even blood concentration of ketone bodies and a significantly longer delivery "tail" of exogenous ketone bodies, such as 1-8 hours after consuming the stacked composition.

S-enantiomer-containing esters and stacked compositions can also modify metabolic function and permit the selection and tailoring of different ratios and combinations of various forms of beta-hydroxybutyrate and acetoacetate to address different nutritional and/or health needs of different individuals or groups. For example, different ratios and/or combinations of different types of exogenous ketone bodies can be selected to address different conditions based on a person's age, gender, state of health, disease condition, and the like.

S-enantiomer-containing esters and stacked compositions described herein may be useful as one or more of: improvements to metabolic function, such as anticonvulsant effects, enhanced metabolism by the brain, neuroprotection, muscle sparing properties, improved cognitive and physical performance, and epigenetic effects (positive or beneficial gene expressions). Science-based improvements in efficiency of cellular metabolism, managed through ketone supplementation, can have beneficial impacts on physical, cognitive health, and psychological health, and a long-term impact on health with respect to the common avoidable diseases such as obesity, insulin resistance, cardiovascular disease, neurodegenerative diseases, diabetes, and cancer, treatment for high blood glucose or type II diabetes, brain tonic, athletic performance enhancer, preventative against metabolic dysfunction, mitochondrial defect, anti-aging supplement, and other uses associated with improved metabolic health.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

BRIEF DESCRIPTION OF DRAWINGS

Various objects, features, characteristics and advantages of the invention will become apparent and more readily appreciated from the following description of the embodiments, taken in conjunction with the accompanying drawings and the appended claims, all of which form a part of this specification wherein like reference numerals designate corresponding parts in the various figures and wherein the various elements depicted are not necessarily drawn to scale, and wherein:

DETAILED DESCRIPTION

I. Definitions

Figure 1A:
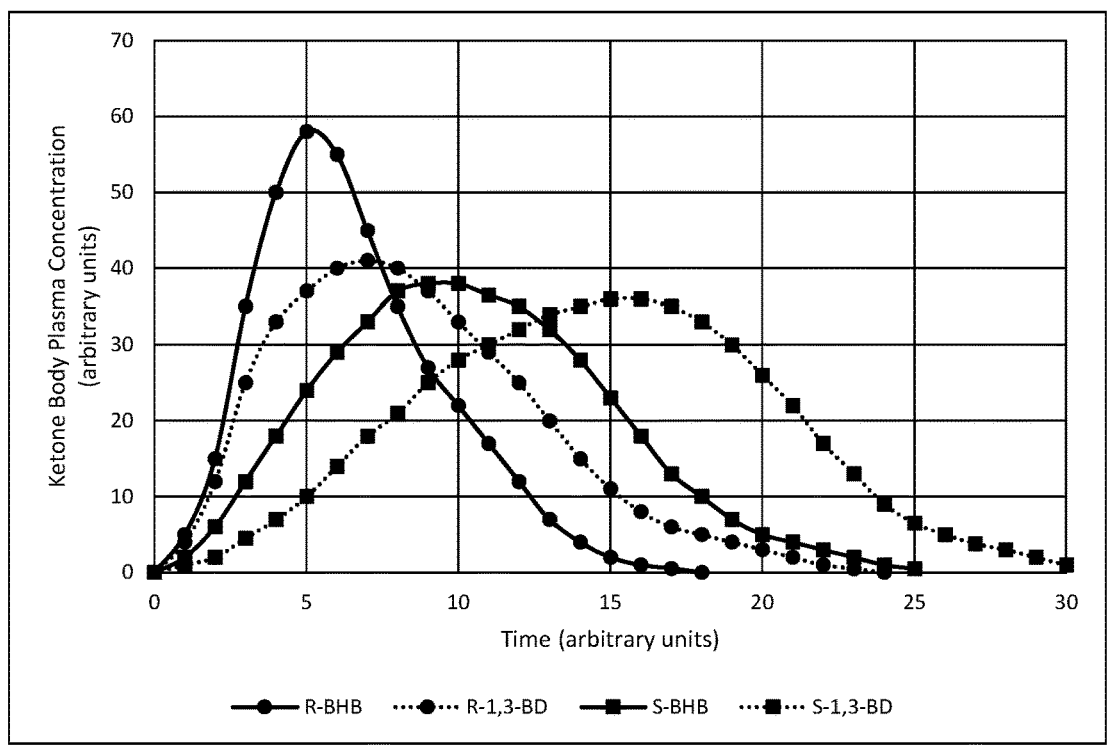
FIG. 1A compares expected pharmacokinetic profiles of R-beta-hydroxybutyrate (R-BHB), R-1,3-butanediol (R-1,3-BD), S-beta-hydroxybutyrate (5-BHB), and S-1,3-butanediol (S-1,3-BD), illustrating that R-beta-hydroxybutyrate and R-1,3-butanediol provide relatively faster maximum concentration peaks and shorter overall duration while S-beta-hydroxybutyrate and S-1,3-butanediol provide relatively later maximum concentration peaks but more sustained overall duration.

The compound "beta-hydroxybutyrate," also known as β-hydroxybutyrate, 3-hydroxybutyrate, βHB, beta-hydroxybutyrate, or beta-hydroxybutyrate, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

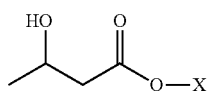

where,

X can be hydrogen, metal ion, amino cation such as from an amino acid, alkyl, alkenyl, aryl, or acyl. The alkyl, alkenyl, aryl, or acyl may be substituted or unsubstituted. For example, an alkyl may include one or more hydroxyl groups.

When X is a hydrogen, the compound is beta-hydroxybutyric acid. When X is a metal ion or an amino cation, the compounds is a beta-hydroxybutyrate salt. When X is alkyl, alkenyl, or aryl (any one of which may be substituted or unsubstituted), the compounds is a beta-hydroxybutyrate ester. When X is acyl (which may be substituted or unsubstituted), the compound is an acid anhydride. The foregoing compounds can be in any desired physical form, such as crystalline, powder, solid, liquid, solution, suspension, or gel.

Beta-hydroxybutyrate may be utilized by a patient's body as an energy source during instances of low glucose levels in the subject or when a patient's body is supplemented with a usable form of beta-hydroxybutyrate. Although not technically a "ketone", one of skill in the art will recognize that beta-hydroxybutyrate, in the context of ketosis, is commonly referred to as a "ketone body".

The beta-hydroxybutyrate compound can be provided as a racemic mixture of enantiomers (i.e., R,S-beta hydroxybutyrate, also known as DL-beta hydroxybutyrate), which can be made synthetically. In humans, R-beta-hydroxybutyrate ("D-3-hydroxybutyrate," "D-beta hydrobutyrate," or "D-beta-hydroxybutyrate") is synthesized in the liver from acetoacetate, the first ketone produced during fasting. In some embodiments it may be desirable to provide beta-hydroxybutyrate as the R-enantiomer to increase potency, either enriched relative to S-beta-hydroxybutyrate ("L-3-hydroxybutyrate," "L-beta hydrobutyrate," or "L-beta-hydroxybutyrate") or in purified form isolated from S-beta-hydroxybutyrate. The general structure of an R-beta-hydroxybutyrate compound is shown below:

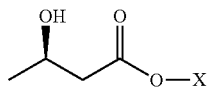

where X is the same as indicated above.

Alternatively, it may be desirable to provide beta-hydroxybutyrate as the S-enantiomer, either enriched relative to R-beta-hydroxybutyrate or in purified form isolated from R-beta-hydroxybutyrate. S-beta-hydroxybutyrate may be associated with one or more of: increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA. The general structure of an S-beta-hydroxybutyrate compound is shown below:

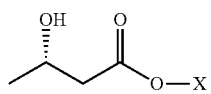

where X is the same as indicated above.

Administering R-beta-hydroxybutyrate, the endogenous form, results in attaining relatively rapid elevated ketosis, while administering S-beta-hydroxybutyrate, which must first be converted to the R form and/or acetoacetate, provides slower and more sustained ketosis and can modify metabolic function in other ways as described herein. The different enantiomers may therefore be combined in different proportions to tailor a desired time release profile according to particular application needs or preferences.

The compound "acetoacetate" is the deprotonated form of acetoacetic acid, which is a carboxylic acid having the formula $CH_3COCH_2COOH$. The deprotonated form present at typical biological pH levels is therefore $CH_3COCH_2COO^-$. As with beta-hydroxybutyrate, acetoacetate may be utilized as an energy source during ketosis. The following general chemical structure represents acetoacetate compounds that may be utilized in the disclosed compositions:

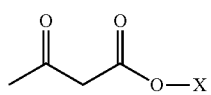

where,

X can be hydrogen, metal ion, amino cation, such as from an amino acid, alkyl, alkenyl, aryl, or acyl. The alkyl, alkenyl, aryl, or acyl may be substituted or unsubstituted. For example, an alkyl may include one or more hydroxyl groups.

When X is a hydrogen, the compound is acetoacetic acid. When X is a metal ion or an amino cation, the compounds is an acetoacetate salt. When X is alkyl, alkenyl, or aryl (any one of which may be substituted or unsubstituted), the compounds is an acetoacetate ester. When X is acyl (which may be substituted or unsubstituted), the compound is an acid anhydride. The foregoing compounds can be in any desired physical form, such as crystalline, powder, solid, liquid, solution, suspension, or gel.

The beta-hydroxybutyrate and acetoacetate compounds described above may be collectively referred to herein as "ketone bodies," "exogenous ketone bodies," a "ketone body component," or "exogenous ketones."

The compound "1,3-butanediol," also known as 1,3-butylene glycol, butane-1,3-diol, or 1,3-dihydroxybutane, is a chiral diol with the general formula $HOCH_2CH_2CH(OH)CH_3$. When administered, 1,3-butanediol undergoes conversion to beta-hydroxybutyrate via first-pass metabolism in the liver. The general chemical structure shown below represents 1,3-butanediol compounds that may be utilized in the disclosed compositions:

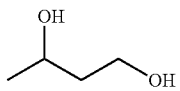

As with beta-hydroxybutyrate, 1,3-butanediol has a stereocenter, and therefore has an R-enantiomer form and an S-enantiomer form. The 1,3-butanediol may be provided as a racemic mixture of enantiomers (i.e., (R,S)-1,3-butandiol). 1,3-butanediol may alternatively be provided as the R-enantiomer, either enriched relative to the S-enantiomer or isolated from the S-enantiomer. R-1,3-butanediol is conventionally believed to be the preferred form since it is directly converted in the liver to R-beta-hydroxybutyrate, which is generally believed to be the only form usable by the body as an energy source. The general structure of R-1,3-butanediol is shown below:

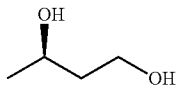

Alternatively, 1,3-butanediol may be provided as the S-enantiomer, either enriched relative to the R-enantiomer or isolated from the R-enantiomer. As explained in more detail below, although S-1,3-butanediol has been conventionally disfavored, there are several benefits associated with its use, particularly for signaling and modifying metabolic function in desirable ways before being converted into beta-hydroxybutyrate. Administering S-1,3-butanediol provides a slow fuse that requires several transformations before it is converted into beta-hydroxybutyrate, thus promoting a sustained, long-term profile for desired circulating levels of ketone bodies and/or providing other beneficial changes to metabolic function. The general structure of S-1,3-butanediol is shown below:

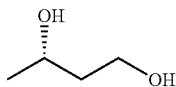

The terms "stacked composition," "keto-stack," "stack," "ketone body stack," variations thereof, and the like are used herein to refer to a composition including at least two separate exogenous ketone bodies selected from the group consisting of: (i) a beta-hydroxybutyrate salt; (ii) an acetoacetate salt; (iii) a beta-hydroxybutyrate ester; (iv) an acetoacetate ester; (v) a beta-hydroxybutyrate free acid (i.e., beta-hydroxybutyric acid); and (vi) an acetoacetate free acid (i.e., acetoacetic acid). Compounds (i) and (ii) represent different forms of "ketone body salts." Compounds (iii) and (iv) represent different forms of "ketone body esters." And compounds (v) and (vi) represent different forms of "ketone body free acids."

In at least some instances, the particular exogenous ketone body (i.e., beta-hydroxybutyrate or acetoacetate) is referred to as the "ketone body component" while the particular salt, ester, or free acid portion is referred to as the "carrier component." For example, a sodium beta-hydroxybutyrate compound utilizes sodium as the carrier component and beta-hydroxybutyrate as the ketone body component, acetoacetic acid utilizes hydrogen as the carrier component and acetoacetate as the ketone body component, and a methyl beta-hydroxybutyrate utilizes a methyl group as the carrier component and beta-hydroxybutyrate as the ketone body component. The ester and/or salt forms of ketone bodies can be thought of as "carriers" for the acid form because they reduce acidity and harshness as compared to pure acid forms.

Some embodiments, in particular those that include a free acid form of an exogenous ketone body, may also include a "stabilizer" that functions to provide the exogenous ketone body in a more administrable form. For example, beta-hydroxybutyric acid and/or acetoacetic acid may be partially neutralized using a strong or weak base, such as an alkali or alkaline earth metal hydroxide, carbonate, or bicarbonate, basic amino acid, and the like. Following such a partial neutralization, the solution will also include a "salt" form as defined herein. But where the neutralization is only partial, and a certain molar excess of W ions remains present, the solution will also include a proportion of the free acid form.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid and/or acetoacetic acid with a strong or weak base, such as an alkali or alkaline earth metal hydroxide, carbonate, or bicarbonate, basic amino acid, and the like.

Exemplary salt forms include sodium, potassium, calcium, and magnesium salts. Some embodiments include one or more transition metal salts. Transition metal cations suitable for use as part of a salt include lithium, chromium, manganese, cobalt, copper, zinc, iron, (e.g., as an iron II or iron III cation), molybdenum, and selenium. Other suitable salt forms include cations of amino acids or their derivatives, such as arginine, lysine, histidine, ornithine, creatine, agmatine, and citrulline.

Suitable ester forms of beta-hydroxybutyrate and acetoacetate include mono-esters of ethanol, mono-esters of 1-propanol, mono- or di-esters of 1,3-propanediol, mono- or di-esters of 1,3-butanediol, and mono-, di-, or tri-esters of glycerin. Particularly preferred embodiments include one or more esters of S-beta-hydroxybutyrate and/or mono- or di-esters of S-1,3-butanediol and one or more ketone bodies (beta-hydroxybutyrate and/or acetoacetate).

As used herein, "subject" or "patient" refers to mammals, including humans and other primates. The subject may be any mammal requiring metabolic therapy, treatment, or prophylaxis, or any mammal suspected of requiring metabolic therapy, treatment, or prophylaxis. Prophylaxis means that regiment is undertaken to prevent a possible occurrence, such as where a high risk of diabetes or other metabolic disorder is identified. "Patient" and "subject" are used interchangeably herein.

The term "unit dose" refers to a dosage form that is configured to deliver a specified quantity or dose of composition or component thereof. Example dosage forms include, but are not limited to, tablets, capsules, powders, food products, food additives, beverages, beverage additives, candies, suckers, pastilles, food supplements, sprays, injectables, and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, spoon, spatula, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on web sites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as scoops, syringes, spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

"Ketosis" as used herein refers to a subject having blood ketone levels within the range of about 0.5 mmol/L to about 16 mmol/L. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis," or it denotes an altered metabolism in which fat becomes the predominant energy source, consequently shifting the body from a state of fat storage to a state of fat oxidation.

The term "medium chain triglycerides" (MCT) refers to molecules having a glycerol backbone attached to three medium chain fatty acids. Medium chain fatty acids range from 6 to 12 carbon atoms in length. Examples of medium chain fatty acids include caproic acid, caprylic acid, capric acid, and lauric acid. Because MCTs are ketone body precursors, including one or more MCTs may provide an additional source for the production of ketone bodies independent of the beta-hydroxybutyrate and acetoacetate compounds, thus helping to promote sustained elevation of ketone levels to a desired therapeutic level.

The term "short chain triglycerides" (SCT) refers to molecules similar to MCT molecules but with short chain fatty acids (less than 6 carbon atoms in length) attached to the glycerol backbone. These can be provided in the form of mono-, di-, and triglycerides, other esters, salts, or free acids. Examples of short chain fatty acids include acetic acid, propionic acid, butyric acid, isobutyric acid, valeric acid, and isovaleric acid.

The term "long chain triglycerides" (LCT) refers to molecules similar to MCT molecules but with long chain fatty acids (more than 12 carbon atoms in length) attached to the glycerol backbone. Examples of saturated long-chain fatty acids include myristic acid, palmitic acid, stearic acid, arachidic acid, behenic acid, lignoceric acid, and cerotic acid.

The term "administration" or "administering" is used herein to describe the process in which the ketogenic compositions are delivered to a subject. The composition may be administered in various ways including oral, intragastric, or parenteral (referring to intravenous and intra-arterial and other appropriate parenteral routes), among others.

II. Ester Forms of S-Beta-Hydroxybutyrate and/or S-1,3-Butanediol

As described above, one of the forms the disclosed compositions may be provided in is a ketone body ester. A ketone body ester can include a beta-hydroxybutyrate ester, an acetoacetate ester, or mixture thereof. In some embodiments, the ketone body component may be provided as mono- or di-esters of 1,3-butanediol, such as R-1,3-butanediol, RS-1,3-butanediol, and/or S-1,3-butanediol. Preferred esters can be made from S-beta-hydroxybutyrate and/or S-1,3-butanediol. Esters of S-beta-hydroxybutyrate can be an ester of any alcohol, such as mono-ester of ethanol, mono-ester of 1-propanol, mono- or di-ester of 1,3-propanediol, mono- or di-ester of 1,3-butanediol, and mono-, di-, or tri-ester of glycerin. Ketone body esters and/or esters of S-1,3-butanediol can be utilized in amounts that provide beneficial epigenetic effects, affecting gene expression, and improvements in metabolic function.

Because 1,3-butanediol (e.g., S-1,3-butanediol) includes two hydroxyl groups, it is capable of forming esters with one or two ketone body compounds. Examples of mono-esters of beta-hydroxybutyrate and 1,3-butanediol are represented below:

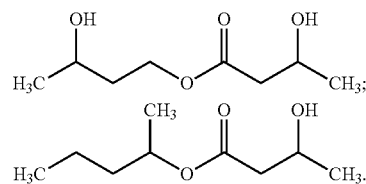

The compounds differ depending on whether the hydroxyl at the 1 position or the 3 position of the 1,3-butanediol forms the ester bond with the carboxyl group of the beta-hydroxybutyrate.

Examples of mono-esters of acetoacetate and 1,3-butanediol (e.g., S-1,3-butanediol) are represented below:

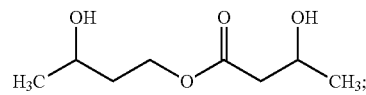

-continued

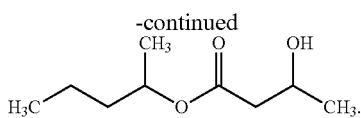

The compounds differ depending on whether the hydroxyl at the 1 position or the 3 position of the 1,3-butanediol forms the ester bond with the carboxyl group of the acetoacetate.

A di-ester of 1,3-butanediol (e.g., S-1,3-butanediol) may include two beta-hydroxybutyrate groups, two acetoacetate groups, or one of each, as shown respectively by the example structures below:

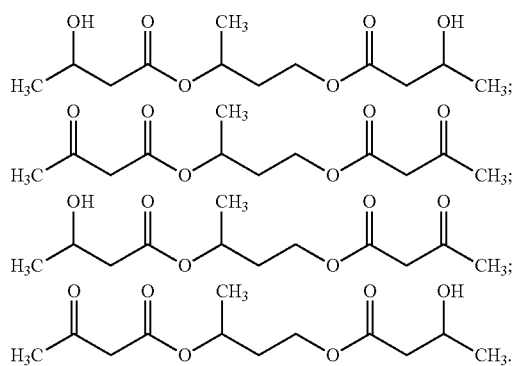

Particularly preferred embodiments include one or more ketone bodies (beta-hydroxybutyrate and/or acetoacetate) as mono- or di-esters of S-1,3-butanediol.

S-beta-hydroxybutyrate and S-1,3-butanediol have conventionally been disfavored as inert at best, or even toxic at worst (see U.S. Pat. No. 8,101,653 to Veech, col. 10, ll. 29-46). However, the inventor of the present disclosure has discovered that controlled delivery of S-beta-hydroxybutyrate esters and/or S-1,3-butanediol as a mono- or di-ester of a ketone body is not only safe but provides several benefits.

Upon administration of S-beta-hydroxybutyrate esters, the S-beta-hydroxybutyrate portion is cleaved from the alcohol component to yield free S-beta-hydroxybutyrate. Upon administration of a mono- or di-ester, S-1,3-butanediol is cleaved from the ketone body component by hydrolysis. It is then converted to S-beta-hydroxybutyrate, which can provide metabolic benefits as described herein in its free form and may be converted endogenously to R-beta-hydroxybutyrate, acetoacetate, fatty acids, and/or sterols. S-1,3-butanediol may also be endogenously converted to R-1,3-butanediol, which is then converted to R-beta-hydroxybutyrate.

Although the metabolic pathway from S-1,3-butanediol to a circulating ketone body is longer than with R-1,3-butanediol, there are several circumstances where a slower, more sustained pharmacokinetic profile is desirable. This is particularly true during a ketogenic diet, where the goal is to maintain a sustained level of circulating ketone bodies in the blood for weeks or months at a time. S-1,3-butanediol can therefore be bonded with acetoacetate and/or with one or both enantiomeric forms of beta-hydroxybutyrate to tailor a pharmacokinetic profile according to particular application needs or preferences. Such esters may also be mixed with R-1,3-butanediol or esters thereof to further modify the pharmacokinetic profile.

FIG. 1A illustrates and compares the expected release profiles of R-beta-hydroxybutyrate (R-BHB), R-1,3-butanediol (R-1,3-BD), S-beta-hydroxybutyrate (S-BHB), and S-1,3-butanediol (S-1,3-BD). As shown, R-beta-hydroxybutyrate raises levels of ketone bodies in the blood relatively faster and to a higher degree, but also tapers off relatively faster. Note that the profile for acetoacetate would be expected to be similar. R-1,3-butanediol also raises blood ketone levels, but to a slower degree than R-beta-hydroxybutyrate because it must first be converted to R-beta-hydroxybutyrate by the liver. S-beta-hydroxybutyrate raises blood ketone levels in an even slower, but more prolonged, manner. Finally, S-1,3-butanediol provides the slowest but longest and most sustained effect on blood ketone levels due to the longer metabolic route required to covert the S-1,3-butanediol to ketone bodies.

Each of the different components are thus expected to provide different pharmacokinetic profiles, each having different benefits and limitations. By combining the different components as esters of beta-hydroxybutyrate and S-1,3-butanediol, the resulting compounds can be made to provide an enhanced overall ketone body release profile. For example, an ester (mono- or di-) of R-beta-hydroxybutyrate, acetoacetate, or S-beta-hydroxybutyrate with S-1,3-butanediol would beneficially combine the relatively faster profiles of R-beta-hydroxybutyrate or acetoacetate, or the mid-range profile of S-beta-hydroxybutyrate, with the relatively more sustained profile of S-1,3-butanediol for an enhanced overall AUC and/or a more tailored and desired pharmacokinetic profile.

Some embodiments may include mixtures of different types of the foregoing esters to further tailor a desired release profile. For example, some embodiments may include a mixture of two or more of: an ester of R-beta-hydroxybutyrate with R-1,3-butanediol; an ester of R-beta-hydroxybutyrate with S-1,3-butanediol; an ester of acetoacetate with R-1,3-butanediol; an ester of acetoacetate with S-1,3-butanediol; an ester of S-beta-hydroxybutyrate with R-1,3-butanediol; and an ester of S-beta-hydroxybutyrate with S-1,3-butanediol. Preferably, at least one of the esters includes one or both of S-beta-hydroxybutyrate or S-1,3-butanediol.

III. Metabolic Effects and Benefits of Acetoacetate, S-Beta-Hydroxybutyrate, and S-1,3-Butanediol Studies shows that exogenous acetoacetate is a ketone body with wide-ranging benefits throughout the body that might be unique to this organic compound. One benefit is improved brain function. Ketones are more than brain food because they can provide protection against certain disease and central nervous system maladies. In one study, treating neurons with 5 mM of acetoacetate protected against cellular toxicity induced by glutamate—a neurotransmitter that contributes to neuronal degeneration and disease.

Acetoacetate is also believed to have superior neuroprotective properties compared to beta-hydroxybutyrate. In mice, administration of an acetoacetate diester delayed central nervous system oxygen toxicity and increased time to seizure. This result can be attributed to increased acetoacetate levels rather than beta-hydroxybutyrate. The same acetoacetate diester was shown to improve motor coordination, learning and memory, and brain synaptic plasticity in mice with a rare neurological disorder. Ketogenic diets have been used for decades to treat epilepsy, and these newer studies are providing evidence that exogenous ketones, particularly acetoacetate, might also have benefits for the brain in other conditions.

Acetoacetate can also provide liver and muscle protection. Macrophages are inflammatory mediators in the body which coordinate tissue repair, remodeling, and fibrosis after cell injury. It has been found that macrophages have the capability to utilize many sources of fuel for energy, including ketone bodies, rather than glucose only. Acetoacetate can be metabolized by liver macrophages and was shown in one study to protect mice against diet-induced liver fibrosis and injury.

Another important function of acetoacetate is as a signaling molecule in the muscle. Studies have indicated that acetoacetate promotes the proliferation and regeneration of muscle satellite cells and recovers muscle strength, muscle integrity, and improves exercise performance in mice. Acetoacetate also reduces the rate of glucose uptake and glycolysis in skeletal muscle, which is evidence for possible performance-enhancing effects of ketone body metabolism due to glycogen sparing during exercise. Additional data show that ketone bodies have intrinsic signaling capacities that in some may impact cellular or organismal metabolism, and in others, may affect processes such as inflammation, which are known to be involved in certain neurological conditions such as Alzheimer's, Parkinson's, and brain cancers. This highlights the importance in further understanding the complex roles of ketone bodies in modulating cellular signaling responses.

Exogenous acetoacetate can be administered to turn off inflammasomes, which can assist people with chronic inflammatory conditions and autoimmune disorders. Exogenous acetoacetate can be administered to turn on histone deacetylase inhibitors (i.e., "HDAC inhibitors"), which inhibit proliferation of tumor cells by inducing cell cycle arrest, differentiation and/or apoptosis. Exogenous acetoacetate can be administered to activate hormones that assist the body in being in an endogenous fat burning state. Exogenous acetoacetate activates the thyroid to produce thyroxine, trigger testosterone production, make organs functions more effectively, make the body more sensitive and less resistant to insulin, thereby reducing the need to produce as much insulin to metabolize sugars, and assisting production of other beneficial hormones.

Figure 1B:
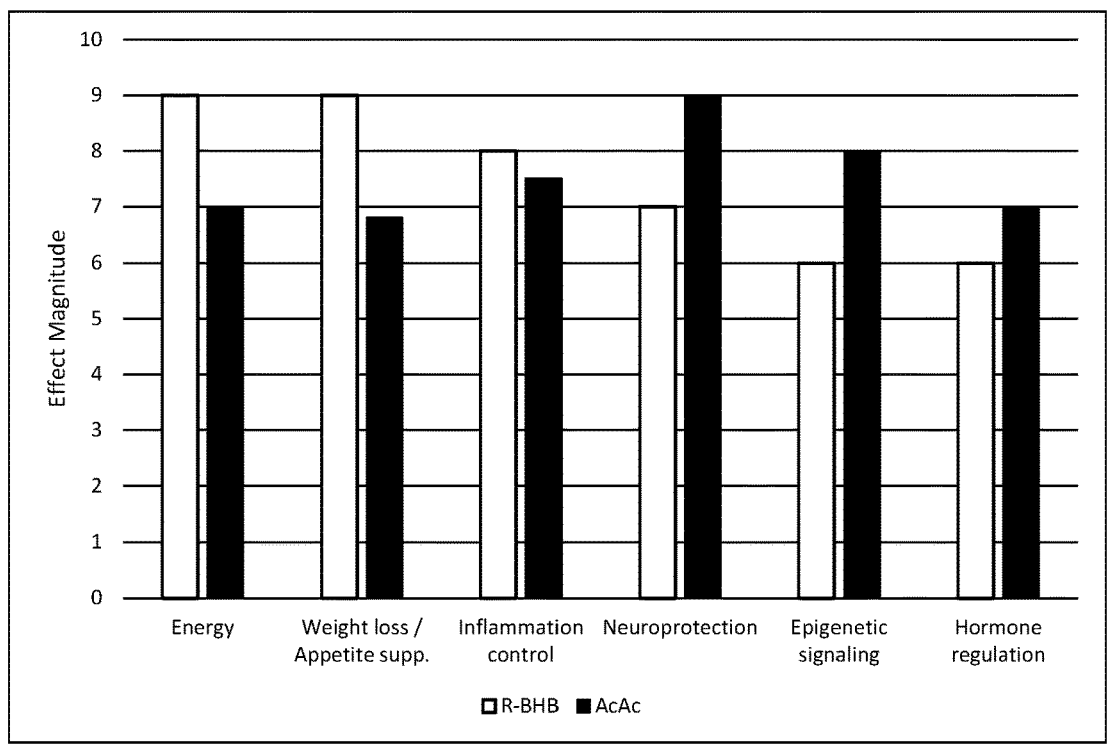
FIG. 1B conceptually illustrates some of the categories of benefits of acetoacetate and R-beta-hydroxybutyrate.

FIG. 1B conceptually illustrates some of the benefits of acetoacetate and R-beta-hydroxybutyrate, showing that (assuming equal amounts) acetoacetate is expected to provide greater effects in several categories of benefits. While R-beta-hydroxybutyrate is extremely useful as an energy source and in applications such as weight loss, appetite suppression, and inflammation control, acetoacetate may have the ability to provide greater effects in other categories such as neuroprotection, beneficial epigenetic signaling, and hormone regulation. However, despite the benefits of acetoacetate, the compound is relatively unstable. A significant portion of exogenously administered acetoacetate tends to decompose into acetone and carbon dioxide. Thus, as a practical matter, the potentially superior benefits of acetoacetate are not realized through exogenous supplementation.

There is evidence that S-beta-hydroxybutyrate is converted into acetoacetate in the liver rather than into R-beta-hydroxybutyrate directly. Thus, S-beta-hydroxybutyrate is likely a direct precursor of acetoacetate such that administering significant quantities of S-beta-hydroxybutyrate is an indirect way of delivering significant quantities of acetoacetate. An advantage of delivering acetoacetate via S-beta-hydroxybutyrate is that S-beta-hydroxybutyrate is much more stable than acetoacetate which, particularly in its acid form, is unstable and decomposes into acetone and carbon dioxide. Whereas some forms of acetoacetate may be stable for only days (e.g., <5 days, 4 days, 3 days, or 2 days), S-beta-hydroxybutyrate can be stable for weeks (>2 weeks, 3 weeks, 4 weeks, or 5 weeks), months (>2 months, 4 months, 6 months, or 8 months), or years (>1 year, 2 years, or 3 years). Such stability assists in manufacture, storage, and consumption of a reliably pure and effective product.

Similarly, S-1,3-butanediol is primarily converted to S-beta-hydroxybutyrate, which is converted into acetoacetate. Thus, S-1,3-butanediol is also a precursor to acetoacetate, albeit requiring an additional transformation. In this case, controlled delivery of significant quantities of S-1,3-butanediol is a way to delivery beneficial acetoacetate. S-1,3-butanediol is also very stable, particularly in ester form together with one or more ketone body components. In the case where S-1,3-butanediol forms a mono- or di-ester with S-beta-hydroxybutyrate, the result is two-stage controlled delivery of acetoacetate, with the S-beta-hydroxybutyrate portion first providing acetoacetate in a controlled and sustained manner as it is converted to acetoacetate and thereafter the S-1,3-butanediol being converted to acetoacetate via conversion into S-beta-hydroxybutyrate. This provides a "molecular stack" rather than a stack mixture, as described herein.

IV. Benefits of Administering Esters of S-Beta-Hydroxybutyrate and/or S-1,3-Butanediol As discussed, many of the metabolic benefits of acetoacetate can be provided by S-beta-hydroxybutyrate to the extent that S-beta-hydroxybutyrate is preferentially converted into acetoacetate rather than R-beta-hydroxybutyrate. Similarly, the metabolic benefits of acetoacetate can be provided by S-1,3-butanediol because it is primarily converted into S-beta-hydroxybutyrate, which is converted into acetoacetate.

Contrary to compositions that deliberately minimize or eliminate S-beta-hydroxybutyrate, compositions described herein are formulated to provide S-beta-hydroxybutyrate directly and/or via S-1,3-butanediol. S-beta-hydroxybutyrate can provide at least one of: (1) increased endogenous production of acetoacetate (and some R-beta-hydroxybutyrate); (2) endogenous conversion of the S-beta-hydroxybutyrate into one or both of R-beta-hydroxybutyrate and acetoacetate; (3) endogenous conversion of the S-beta-hydroxybutyrate into fatty acids and sterols; (4) prolonged ketosis; (5) metabolism of the S-beta-hydroxybutyrate independent of conversion to R-beta-hydroxybutyrate and/or acetoacetate; (6) increased fetal development; (7) increased growth years; (8) reduced endogenous production of acetone during ketosis; (9) signaling by the S-beta-hydroxybutyrate that modulates metabolism; (10) antioxidant activity; and (11) production of acetyl-CoA.

The compositions described herein, having S-beta-hydroxybutyrate and/or S-1,3-butanediol, can be used, for example, to produce one or more desired effects in the subject, including but not limited to, appetite suppression, weight loss, fat loss, reduced blood glucose level, improved mental alertness, increased physical energy, improved cognitive function, reduction in traumatic brain injury, reduction in effect of diabetes, improvement of neurological disorder, inhibition of cancer, reduction of inflammation, anti-aging, antiglycation, reduction in epileptic seizure, improved mood, increased strength, increased muscle mass, or improved body composition.

Figure 1C:
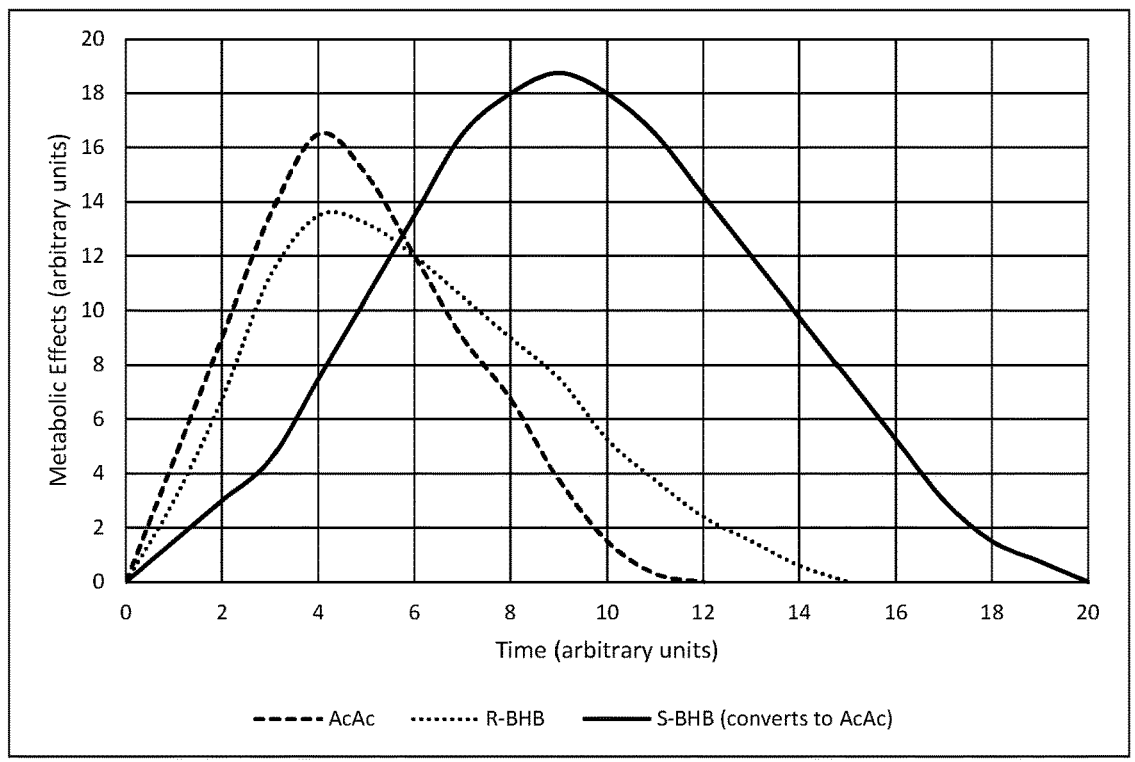
FIGS. 1C and 1D conceptually illustrate comparative benefits of the different components of ester compositions, with FIG. 1C focusing on the effects of the different forms of ketone bodies that can be selected for the ester, and FIG. 1D focusing on the effects of the different forms of 1,3-butanediol that can be selected for the ester.
Figure 1D:
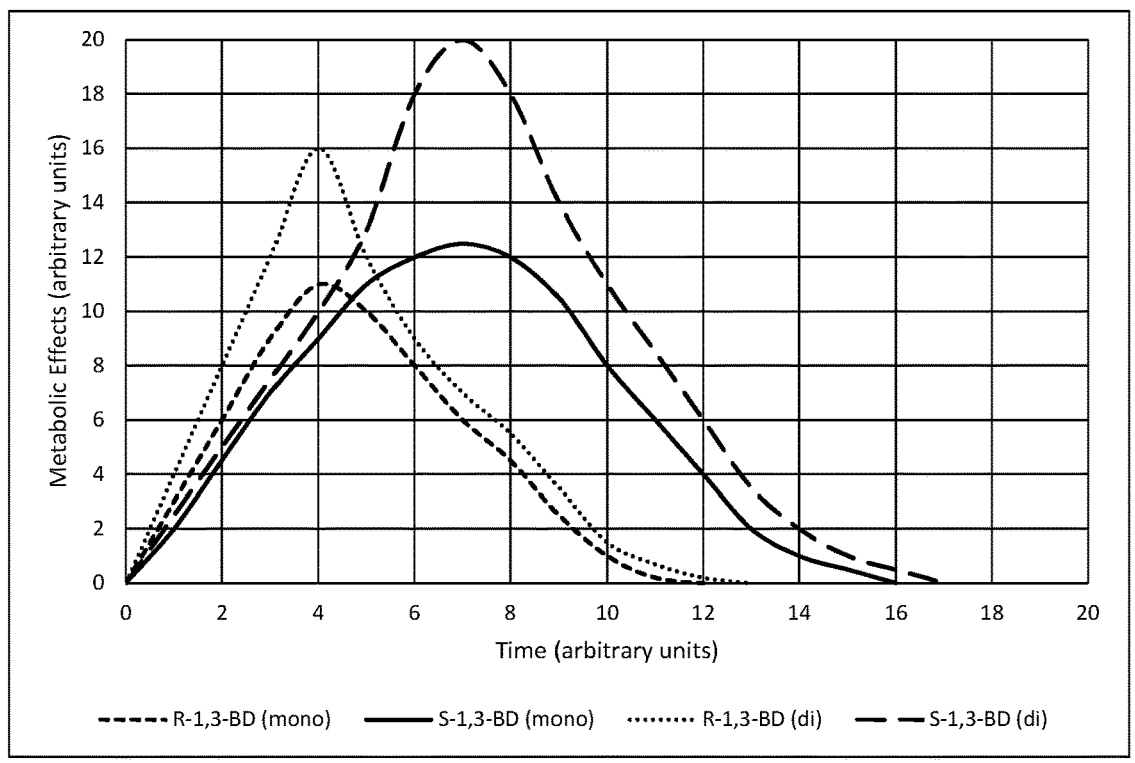

FIGS. 1C and 1D conceptually illustrate comparative benefits of the different components of ester compositions. FIG. 1C focuses on the effects of the different forms of ketone bodies that can be selected for the ester (assuming the 1,3-butanediol component is held constant), while FIG. 1D focuses on the effects of the different forms of 1,3-butanediol that can be selected for the ester (assuming the ketone body component is held constant).

FIG. 1C conceptually illustrates comparative benefits of S-beta-hydroxybutyrate, R-beta-hydroxybutyrate, and acetoacetate over time (assuming administration of an otherwise similar dose). The y-axis represents "metabolic effects", which is used to refer generally to the benefits described herein other than those associated with the direct energy source, weight loss, or appetite suppression functions of ketone bodies. Such benefits are described elsewhere herein and include, for example, neuroprotection, epigenetic signaling, liver protection, inflammation control, hormone regulation, blood glucose control, improved cognitive function, improved mental alertness, and mood control.

As shown in FIG. 1C, the effects of the acetoacetate typically happen faster but have limited duration because much of the dose is quickly utilized by the body as an energy source and a significant amount is also lost due to spontaneous conversion to acetone and $CO_2$. The R-beta-hydroxybutyrate ester provides somewhat lower effects, but the effects last slightly longer than acetoacetate. This is because although the R-beta-hydroxybutyrate ester is more stable than acetoacetate, it is still rapidly utilized by the body as an energy source. On the other hand, the S-beta-hydroxybutyrate ester may be somewhat slower in reaching peak effects, but because S-beta-hydroxybutyrate is not utilized directly as an energy source, and instead must be converted to acetoacetate, the peak magnitude of effects is higher and the duration of effects is much more sustained relative to the other types of esters.

FIG. 1D illustrates comparative benefits of S-1,3-butanediol and R-1,3-butanediol over time (assuming administration of an otherwise similar dose). The y-axis represents "metabolic effects" as used in FIG. 1C. As shown, the effects of the R-1,3-butanediol may be somewhat more rapid, but the R-1,3-butanediol converts to R-beta-hydroxybutyrate which is then quickly utilized as an energy source. On the other hand, the S-1,3-butanediol is first converted to S-beta-hydroxybutyrate (and then to acetoacetate and/or R-beta-hydroxybutyrate), so the duration of effects is more sustained relative to an R-1,3-butanediol ester.

FIG. 1D also shows that diesters of the 1,3-butanediol components may be utilized. The diesters are expected to differ from the mono-esters by providing a higher initial spike in effect magnitude as a result of doubling the ketone body content.

Taking the effects of different ester types shown in FIGS. 1C and 1D, different combinations of esters may be formed by combining a ketone body component (from FIG. 1C) with a 1,3-butandiol component (from FIG. 1D) to provide desired overall effects. An ester that incorporates one or both of S-beta-hydroxybutyrate or S-1,3-butanediol would thus provide higher and more sustained metabolic effects, with an ester of S-beta-hydroxybutyrate and S-1,3-butanediol providing the highest and most sustained effect.

The beneficial use of different types of molecules (a ketone body component and a 1,3-butanediol component) represents a strategy of "molecular stacking". As mentioned above, the 1,3-butanediol component may also form diesters. In other words, two ketone body components may be combined with the 1,3-butandiol component. This represents another form of molecular stacking. These strategies of molecular stacking may also be used in conjunction with the other forms of stacking described herein (e.g., stacking at least two of acid, salt, and ester forms).

V. Balancing Beta-Hydroxybutyrate and Acetoacetate

Certain embodiments are formulated to provide a therapeutically effective amount of beta-hydroxybutyrate and acetoacetate. Beneficially, a combined beta-hydroxybutyrate/acetoacetate composition is formulated to provide biologically balanced proportions of beta-hydroxybutyrate and acetoacetate in order to optimize the induction and/or sustainment of a ketogenic state in the user. For example, the combined beta-hydroxybutyrate/acetoacetate embodiments disclosed herein are capable of more effectively inducing and/or sustaining ketosis in a mammal as compared to an otherwise similar dosage regimen of beta-hydroxybutyrate alone or acetoacetate alone. Likewise, certain of the combined beta-hydroxybutyrate/acetoacetate embodiments disclosed herein are capable of more effectively inducing and/or sustaining ketosis in a mammal as compared to a composition that includes some unspecified amount of acetoacetate (likely some trivial amount).

Figure 2:
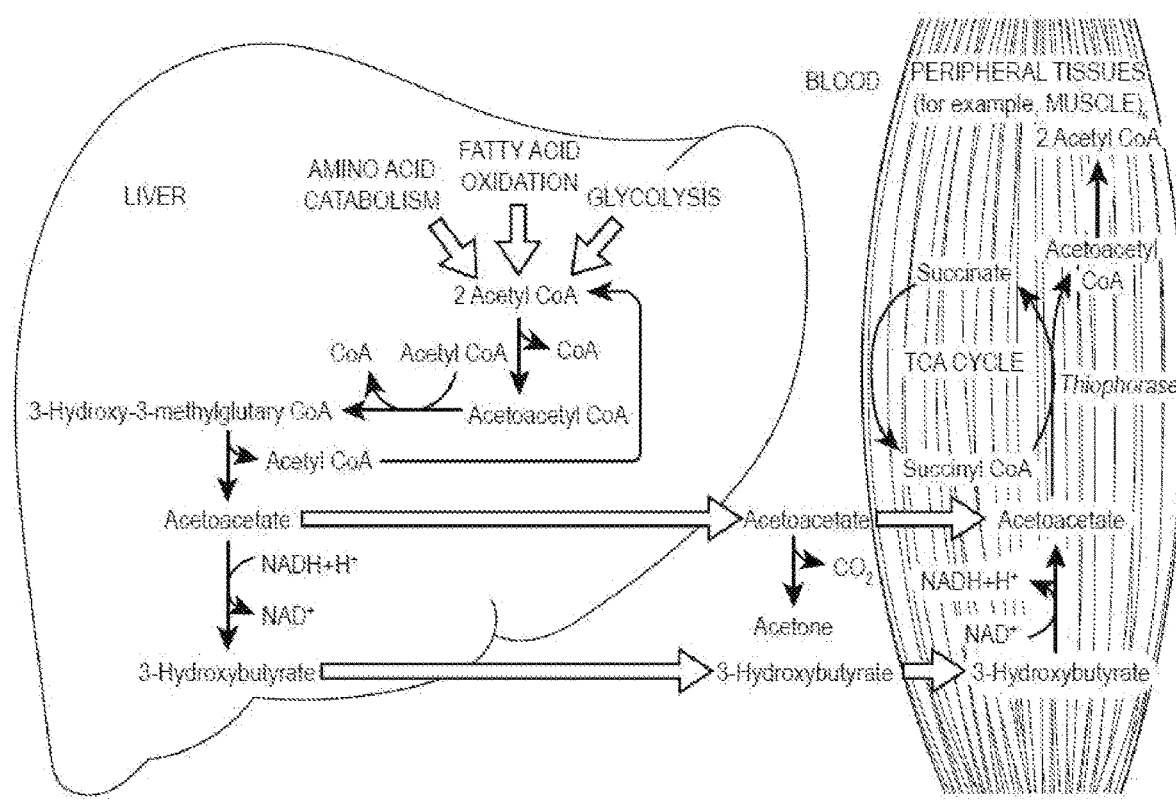
FIG. 2 schematically illustrates some of the metabolic pathways of ketosis, showing ketogenesis in the liver and ketolysis in peripheral tissues such as muscle.

FIG. 2 schematically illustrates the interplay between ketogenesis and ketolysis. Ketogenesis occurs in the liver, where a combination of catabolic processes breaks down amino acids, fatty acids, and/or glycogen to generate the ketone bodies acetoacetate and beta-hydroxybutyrate. The majority of these ketone bodies will typically be produced through fatty acid oxidation.

Although beta-hydroxybutyrate is the more reduced compound, both beta-hydroxybutyrate and acetoacetate are passed into the bloodstream and delivered to peripheral tissues to be used as an energy source. As shown, acetoacetate may be directly utilized in the TCA cycle (i.e., citric acid cycle), whereas beta-hydroxybutyrate is first oxidized by $NAD^+$ into acetoacetate before the resulting acetoacetate is incorporated into the TCA cycle.

With reference again to FIG. 2, the benefits of the combined beta-hydroxybutyrate/acetoacetate compositions described herein will be explained, in particular with regards to the benefits of $NAD^+$ sparing. When a subject is in ketosis, the energy profile is already favorable for $NAD^+$ sparing as compared to when glucose is primarily used for energy. Stacking the separate ketone body components beta-hydroxybutyrate and acetoacetate can beneficially further spare $NAD^+$, as explained below.

As shown, during ketolysis, the available acetoacetate is directly incorporated into the TCA cycle and does not need to be initially oxidized by an $NAD^+$ molecule. During endogenous ketosis (e.g., as a result of fasting), the use of these $NAD^+$ molecules to convert beta-hydroxybutyrate to acetoacetate in peripheral tissues (ketolysis) is essentially balanced by the countervailing generation of $NAD^+$ molecules to convert acetoacetate to beta-hydroxybutyrate in the liver (ketogenesis).

However, when a user is supplementing with exogenous beta-hydroxybutyrate, the use of $NAD^+$ in the peripheral tissues is not balanced in the same way by the generation of $NAD^+$ in the liver. Supplementation of exogenous beta-hydroxybutyrate therefore creates an increase in $NAD^+$ demand on the user. Low levels of $NAD^+$ are associated with aging and declining mitochondrial function. In addition, low $NAD^+$ relative to NADH can set in motion some of the same physiological responses to low NAD$^+$ associated with low oxygen levels, even if actual oxygen levels are accurate.

An exogenous ketogenic composition with an increased proportion of acetoacetate relative to beta-hydroxybutyrate can therefore reduce the depletion of NAD$^+$ as compared to a composition having higher levels of beta-hydroxybutyrate. Compositions described herein include effective levels of acetoacetate in combination with beta-hydroxybutyrate in order to achieve these benefits.

In general, beta-hydroxybutyrate is the primary "energy" ketone body, and having too high of a ratio of acetoacetate to beta-hydroxybutyrate may restrict the ability to obtain a desired energy boost. In some cases, excessive acetoacetate can also introduce undesirable effects. Referring again to FIG. 2, an amount of acetoacetate circulating in the blood can spontaneously convert to $CO_2$ and acetone. High levels of acetone can be undesirable. Elevated acetone levels can, for example, represent inefficient use of energy by indicating that acetoacetate is not being converted to beta-hydroxybutyrate or being appropriately used in the TCA cycle. Further, although the human body is typically able to manage normal ketosis-related acetone levels, physiologically clearing excess acetone can be taxing on the liver. In addition to these primary physiological impacts, excess acetone an also cause unpleasant "keto breath." Exogenous beta-hydroxybutyrate supplementation minimizes acetone generation because beta-hydroxybutyrate is typically not converted into acetoacetate until reaching the peripheral tissues where it is used.

For these reasons, the benefits of increasing the levels of acetoacetate relative to beta-hydroxybutyrate must be balanced against the detrimental effects of excessive acetoacetate. In one embodiment, a ketogenic composition includes a combination of beta-hydroxybutyrate and acetoacetate, with the acetoacetate being included in an amount that is at least about 5%, at least about 10%, at least about 20%, at least about 30%, or at least about 40% w/w of the beta-hydroxybutyrate and acetoacetate mixture.

At the same time, an optimized balance of beta-hydroxybutyrate and acetoacetate is typically where acetoacetate component is limited to no more than about 45% of the beta-hydroxybutyrate and acetoacetate mixture. In other words, an optimized weight ratio of beta-hydroxybutyrate to acetoacetate may be about 19:1, about 16:1, about 14:1, about 12:1, about 9:1, about 6:1, about 4:1, about 3:1, about 7:3, about 1.5:1, about 1.22:1, and ranges defined by these ratios. Formulations having these ratios beneficially ensure that there is sufficient acetoacetate in proportion to the beta-hydroxybutyrate to provide the effective ketogenic properties described herein without causing the detrimental effects associated with excess acetoacetate. Regulating the amount of each separate ketone body component beneficially allows for tailored compositions that are optimized for particular needs or preferences. As described in more detail below, the relative amounts of beta-hydroxybutyrate and acetoacetate may be adjusted and optimized based on a subject's age, health, activity level, desired dosage regimen, and/or liver sensitivity, for example.

In general, subjects that may be deficient in NAD+, such as more elderly (e.g., those over 55, those over 60, those over 65, or those over 70) or infirm people, may benefit from higher relative amounts of acetoacetate, such as between about 25% to about 45% acetoacetate, or about 30% to about 45% acetoacetate, or about 35% to about 45% acetoacetate of the beta-hydroxybutyrate and acetoacetate mixture. In addition, the compositions disclosed herein may contain supplemental NAD+.

Similarly, subjects that are not deficient in NAD+, such as healthier, younger people, may benefit from lower relative amounts of acetoacetate, such as between about 5% to about 25% acetoacetate, or about 8% to about 22% acetoacetate, or about 10% to about 20% acetoacetate of the beta-hydroxybutyrate and acetoacetate mixture.

VI. Stacking Different Ketone Bodies, Ketone Body Forms, and Precursors

As described above, the exogenous ketone bodies described herein may be provided in three general forms: 1) salt form, 2) ester form, and 3) free acid form (i.e., beta-hydroxybutyric acid or acetoacetic acid). Beta-hydroxybutyric acid can be provided as the R-enantiomer, S-enantiomer, racemic mixture, or enriched with the R- or S-enantiomer. The compositions described herein may be provided in any one of these forms or as a "stacked" mixture combining at least two of these forms. Stacking different ketone bodies, ketone body forms, and precursors permits one to design an ideal stack for a particular recipient (e.g., based on age, health condition, gender, etc.) to improve metabolic function.

Each of the different forms has its own properties and its own potential benefits and limitations. For example, ester forms of beta-hydroxybutyrate or acetoacetate typically have poor organoleptic properties relative to the other forms. For example, ester forms of beta-hydroxybutyrate or acetoacetate are often described as having a pungent taste and/or smell.

Salt forms of beta-hydroxybutyrate or acetoacetate are generally considered to taste better than ester forms. However, administration of clinically or dietetically effective doses of exogenous ketone bodies in salt form inherently requires administration of relatively high levels of the corresponding cations. Sodium, for example, is often used as the cation in ketone body salts, and high levels of sodium have well-known negative health effects. Excessive amounts of potassium and calcium should also be avoided. Although different salts having different cations may be mixed to dilute the impact of a single cation, it can still be difficult to provide effective amounts of beta-hydroxybutyrate and/or acetoacetate without upsetting the electrolyte balance in the subject/patient.

The free acid forms may also be utilized. However, because beta-hydroxybutyric acid has a pKa of 4.70, it deprotonates and produces H$^+$ at physiological pH. Similarly, acetoacetic acid has a pKa of 3.59 and likewise deprotonated and produces H$^+$ at physiological pH. The resulting excess acidity can cause undesirable side effects including causing or aggravating gastrointestinal issues such as ulcers or reflux.

The free acid form of acetoacetate is the least stable form (meaning that it can decompose to acetone and carbon dioxide), with the salt form being somewhat more stable and the ester form being significantly more stable. The acid form has a half-life of 140 minutes at 37° C. in water, whereas the basic form (the anion in a salt form) has a half-life of 130 hours. That is, it decomposes about 55 times more slowly. Esters are far more stable and can persist for weeks, months, or years depending on storage conditions.

Combining different forms of exogenous ketone bodies can beneficially limit the occurrence and/or severity of these undesirable side-effects and/or can permit administration of higher doses of exogenous ketone bodies. For example, a ketone body stack can deliver the same amount of exogenous ketones as a single form without causing the same occurrence and/or severity of side-effects. Likewise, a combined form can deliver a greater amount of exogenous ketones than a single form before reaching similar occurrence and/or severity of side-effects.

Figure 3A:
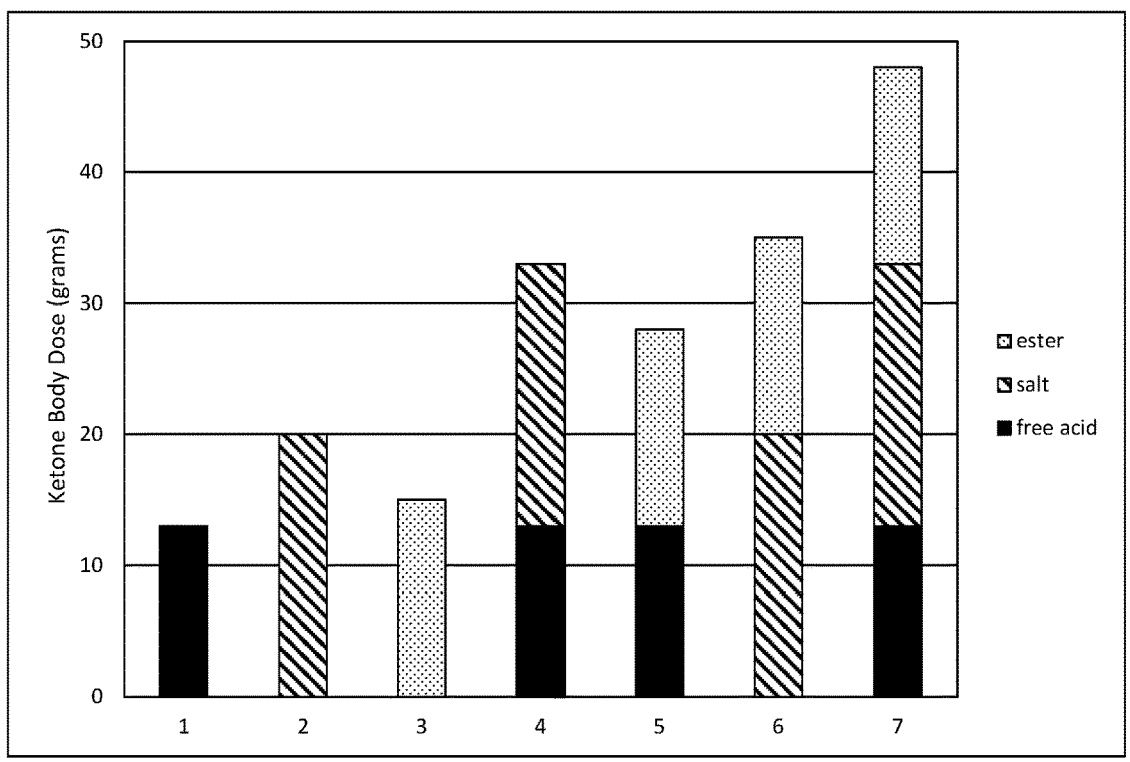
FIG. 3A illustrates higher levels of exogenous ketone bodies that may be administered when using a "stacked" dose of at least two different forms of exogenous ketone bodies as compared to single forms of the exogenous ketone body.
Figure 3B:
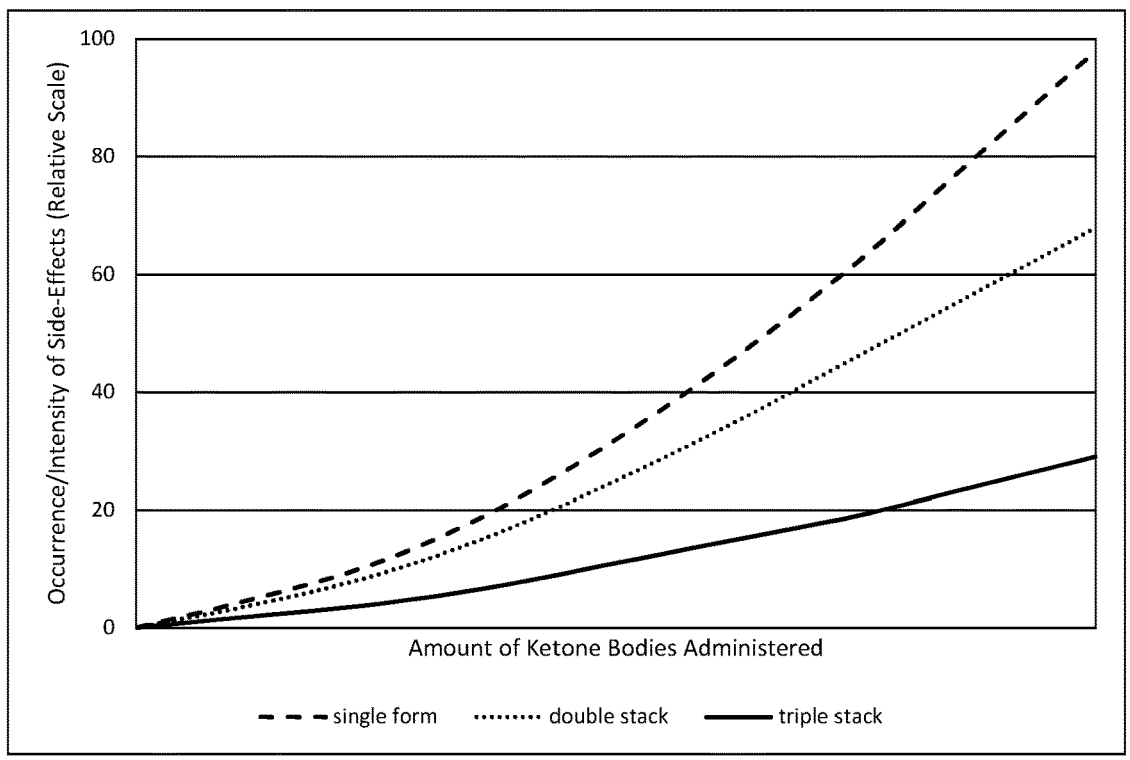
FIG. 3B illustrates expected relative rates of undesirable side-effects resulting from treatment with various formulations of exogenous ketone bodies.

This is schematically illustrated in FIGS. 3A and 3B. FIG. 3A shows different exogenous ketone doses when using a single form (formulations 1-3), a double stack (formulations 4-6), and a triple stack (formulation 7). Although individual tolerances may vary and the illustrated doses are therefore exemplary only, a typical subject will want to avoid excessive amounts of any single form of exogenous ketones in order to avoid the corresponding side effects.

Accordingly, stacking different forms of exogenous ketones allows for greater delivery of exogenous ketones in a dose and/or allows for a higher dosing frequency as compared to use of the single form. For example, different forms of exogenous ketones may be stacked in a single dose to allow for greater amounts of exogenous ketones in the dose, and/or different forms of exogenous ketones may be taken in different doses throughout the day to allow for greater dosing frequency and thus higher overall daily delivery of exogenous ketones.

A single dose of stacked ketones can also provide more sustained levels of ketone bodies in the blood as compared to an otherwise similar amount provided in a single form. For example, a stacked formulation can be tailored to provide a more preferable release profile, such as one that combines the benefits of more rapid onset with the benefits of a more extended release, and/or one that provides an overall greater pharmacokinetic AUC.

FIG. 3B shows expected relative severity of undesirable side-effects resulting from treatment with various formulations of exogenous ketones, including stacked formulations. The triple stack formulation comprising each of 1) a salt form of an exogenous ketone, 2) an ester form of an exogenous ketone, and 3) a free acid form of an exogenous ketone is expected to allow for administration of a greater amount of exogenous ketones and/or to have reduced side-effects as compared to a double stack comprising only two such forms of exogenous ketones. Both the triple stack and the double stack are likewise expected to allow for administration of a greater amount of exogenous ketones and/or to have reduced side-effects as compared to a single form comprising only one form of exogenous ketone.

In other words, for a given dose of exogenous ketones, the triple stack can be formulated to cause less 1) organoleptic side-effects, 2) electrolyte imbalance side-effects, and/or 3) acidity side-effects as compared to the double stack or single form. For example, a single form ketones body ester may have a threshold dosage that the typical user will not exceed because of the negative organoleptic side-effects, a single form ketone body salt may have a threshold dosage limited by the recommended dietary limits of the electrolytes administered with the salt, and a single form ketone body free acid may have a threshold dosage that the typical user will not exceed because of the negative effects of acidity. The stacked forms of exogenous ketones, and in particular the exogenous ketone triple stack, allows for supplementation of greater amounts of exogenous ketones without passing any of the separate thresholds related to organoleptic, electrolyte, or acidity side-effects. It also helps with metabolic function.

Stacks that contain R-beta-hydroxybutyrate will provide additional energy, particularly in the bodies utilization of ketone bodies for energy instead of or in addition to sugars. Stacks that contain acetoacetate can provide the metabolic benefits discussed above, such as signaling and gene expression. Stacks that contain S-beta-hydroxybutyrate can provide their own unique signaling function, such as appetite suppression, and also the beneficial affects of acetoacetate when S-beta-hydroxybutyrate is converted to acetoacetate. Stacks that contain 5-1.3-butanediol provide a slow fuse for primarily obtaining the desirable benefits of S-beta-hydroxybutyrate and acetoacetate, although some 5-1.3-butanediol may ultimately be converted to R-beta-hydroxybutyrate and provide additional energy as a ketone body.

In some embodiments, a beta-hydroxybutyrate stack includes at least two of: (i) one or more exogenous ketone salts; (ii) one or more exogenous ketone esters; and (iii) an exogenous ketone body acid (beta-hydroxybutyric acid and/or acetoacetic acid). For example, an exogenous ketone double stack may include at least two of components (i), (ii), and (iii) each provided at about 2% to about 98%, or about 5% to about 95%, or about, 10% to about 90%, or about 20% to about 80%, or about 30% to about 70%, or about 40% to about 60% on a molar basis of the ketone body component.

In some embodiments, a ketone body triple stack includes a ketone body ester at about 2% to about 96%, or about 5% to about 90%, or about 10% to about 80%, or about 20% to about 60% on a molar basis of the ketone body component, includes a ketone body salt at about 2% to about 96%, or about 5% to about 90%, or about 10% to about 80%, or about 20% to about 60% on a molar basis of the ketone body component, and includes a free acid form at about 2% to about 96%, or about 5% to about 90%, or about 10% to about 80%, or about 20% to about 60% on a molar basis of the ketone body component. In some embodiments, a triple stack includes each of the three carrier component forms in substantially equal amounts on a molar basis of the ketone body component.

A ketone body stack may also provide a more beneficial digestive release profile. Each of the different carrier component forms may interact somewhat differently upon ingestion. For example, the free acid form may be readily delivered to the bloodstream as a usable ketone body, whereas ketone bodies from salt forms may in general take slightly longer to reach the bloodstream depending on the solubility characteristics of the particular salt or salt mixture utilized, and ester forms may in general take the longest to reach the bloodstream depending on how rapidly the ester bond undergoes hydrolysis. Thus, a stacked formulation can be tailored to provide a more preferable release profile, such as one that combines the benefits of more rapid onset with the benefits of a more extended release, and/or one that provides an overall greater pharmacokinetic AUC.

Figure 4:
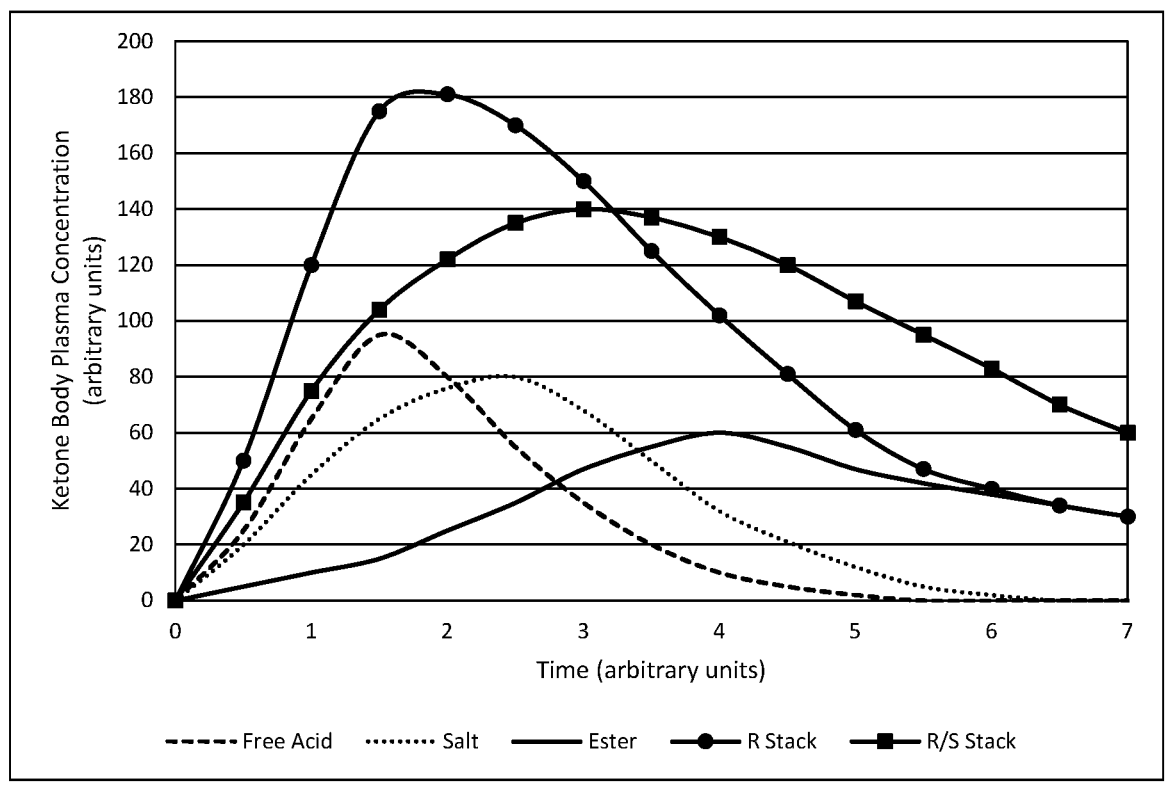
FIG. 4 compares expected pharmacokinetic profiles of stacked compositions (e.g., R-beta-hydroxybutyrate comprising each of the free acid, salt, and ester forms and R,S-beta-hydroxybutyrate) to each of the free acid, salt, and ester single forms, illustrating that stacked compositions may provide an overall release profile that is extended and has a larger area under the curve (AUC).

This is illustrated in FIG. 4, which compares expected release profiles of keto stack compositions (e.g., comprising each of the free acid, salt, and ester forms) to each of the free acid, salt, and ester single forms. Because the keto stack compositions are able to provide more overall exogenous ketone bodies, and because they are provided in a plurality of different forms with different release characteristics, the overall release profile is extended and provides a larger AUC.

FIG. 4 also illustrates how a release profile may be adjusted by utilizing different relative amounts of S-beta-hydroxybutyrate and R-beta-hydroxybutyrate. As illustrated, the beta-hydroxybutyrate in the "R Stack" is substantially comprised of R-beta-hydroxybutyrate, while the "R/S Stack" replaces some of the R-beta-hydroxybutyrate with S-beta-hydroxybutyrate to flatten and extend the release profile.

Given that there are three separate "carrier component" forms and two different "ketone body component" types, there are multiple keto stack combinations that may be formulated. As reproduced below, Table 1 illustrates several exemplary stacked combinations having 2, 3, 4, 5, or 6 different compound types making up the stack.

TABLE 1

| Combo No. | BHB Salts | BHB Ester | BHB Acid | ACAC Salt | ACAC Ester | ACAC Acid |
|---|---|---|---|---|---|---|
| 2-part stacks | | | | | | |
| 1 | x | x | | | | |
| 2 | x | | x | | | |
| 3 | x | | | x | | |
| 4 | x | | | | x | |
| 5 | x | | | | | x |
| 6 | | x | x | | | |
| 7 | | x | | x | | |
| 8 | | x | | | x | |
| 9 | | x | | | | x |
| 10 | | | x | x | | |
| 11 | | | x | | x | |
| 12 | | | x | | | x |
| 13 | | | | x | x | |
| 14 | | | | x | | x |
| 15 | | | | | x | x |
| 3-part stacks | | | | | | |
| 16 | x | x | x | | | |
| 17 | x | x | | x | | |
| 18 | x | x | | | x | |
| 19 | x | x | | | | x |
| 20 | | x | x | x | | |
| 21 | | x | x | | x | |
| 22 | | x | x | | | x |
| 23 | | | x | x | x | |
| 24 | | | x | x | | x |
| 25 | x | | x | x | | |
| 26 | | | x | x | x | |
| 4-part stacks | | | | | | |
| 27 | x | x | x | x | | |
| 28 | x | x | x | | x | |
| 29 | x | x | x | | | x |
| 30 | | x | x | x | x | |
| 31 | | x | x | x | | x |
| 32 | | | x | x | x | x |
| 33 | | x | x | | x | x |
| 34 | x | x | | | x | x |
| 35 | x | x | | x | | x |
| 5-part stacks | | | | | | |
| 36 | x | x | x | x | x | |
| 37 | x | x | x | x | | x |
| 38 | | x | x | x | x | x |
| 39 | x | | x | x | x | x |
| 40 | x | x | | x | x | x |
| 6-part stack | | | | | | |
| 41 | x | x | x | x | x | x |

VII. Administration

Ketogenic compositions described herein may be administered to a subject in therapeutically effective dosages and/or in frequencies to induce or sustain ketosis. The combined beta-hydroxybutyrate and acetoacetate mass in a daily dose may range from about 0.5 gram to about 50 grams, or about 0.75 gram to about 25 grams, or about 1 gram to about 15 grams, or about 1.5 grams to about 12 grams.

In some embodiments, the compositions may further include one or more medium chain fatty acids, fatty acid esters, or mono-, di- or triglycerides of medium chain fatty acids in order to provide an additional source of ketone bodies for sustaining ketosis for a longer period of time compared to if just the beta-hydroxybutyrate/acetoacetate combination were used by itself. In some embodiments, the composition is preferably administered such that the ratio of beta-hydroxybutyrate/acetoacetate to medium chain fatty acid (or ester thereof) ranges from about 4:1 to about 1:4, or from about 2:1 to about 1:2, or from about 1.5:1 to about 1:1.5.

In alternative embodiments, the compositions may further include one or more short and/or long chain fatty acids, fatty acid esters, or mono-, di- or triglycerides of short and/or long chain fatty acids in order to provide an additional source of ketone bodies for sustaining ketosis. In some embodiments, the composition is preferably administered such that the ratio of beta-hydroxybutyrate/acetoacetate to medium, short and/or long chain fatty acid (or ester thereof) ranges from about 4:1 to about 1:4, or from about 2:1 to about 1:2, or from about 1.5:1 to about 1:1.5.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, a ketogenic composition is administered via oral administration of the composition in a solid, powdered form or liquid, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etcetera.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of the composition components, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once over a given time period (e.g., once per day), or may be divided and administered over intervals of time. It is to be understood that administration may be adjusted according to individual need and professional judgment of a person administrating or supervising the administration of the compositions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition for increasing ketone body level and modify metabolic function in a subject, the composition comprising:
    a mono- or di-ester of:
        a ketone body component selected from beta-hydroxybutyrate, acetoacetate, or both; and
        S-1,3-butanediol; and
    at least one ketone body salt selected from the group consisting of beta-hydroxybutyrate salts and acetoacetate salts.

2. The composition of claim 1, wherein the ketone body component includes R-beta-hydroxybutyrate.

3. The composition of claim 1, wherein the ketone body component is enriched in R-beta-hydroxybutyrate relative to S-beta-hydroxybutyrate.

4. The composition of claim 1, wherein the ketone body component includes S-beta-hydroxybutyrate.

5. The composition of claim 1, wherein the ketone body component is enriched in S-beta-hydroxybutyrate relative to R-beta-hydroxybutyrate.

6. The composition of claim 1, wherein the composition comprises a di-ester having two beta-hydroxybutyrate compounds bonded to the S-1,3-butanediol.

7. The composition of claim 6, wherein both of the beta-hydroxybutyrate compounds are R-beta-hydroxybutyrate.

8. The composition of claim 6, wherein both of the beta-hydroxybutyrate compounds are S-beta-hydroxybutyrate.

9. The composition of claim 6, wherein one of the beta-hydroxybutyrate compounds is R-beta-hydroxybutyrate and another one is S-beta-hydroxybutyrate.

10. The composition of claim 1, wherein the composition comprises a di-ester having two acetoacetate compounds bonded to the S-1,3-butanediol.

11. The composition of claim 1, wherein the composition comprises a di-ester having a beta-hydroxybutyrate and an acetoacetate bonded to the S-1,3-butanediol.

12. The composition of claim 11, wherein the beta-hydroxybutyrate is R-beta-hydroxybutyrate.

13. The composition of claim 11, wherein the beta-hydroxybutyrate is S-beta-hydroxybutyrate.

14. The composition of claim 1, wherein the composition includes a mixture of ketone body components that form the mono- or di-ester such that about 55% to about 95% by weight of ketone bodies of the ketone body component are beta-hydroxybutyrate and about 5% to about 45% by weight are acetoacetate.

15. The composition of claim 1, wherein the at least one ketone body salt includes at least one of a sodium salt, potassium salt, magnesium salt, calcium salt, amino acid salt, or combination thereof.

16. The composition of claim 1, further comprising a carrier, the carrier comprising a powder, liquid, gel, suspension, tablet, capsule, food product, food additive, beverage, beverage additive, or food supplement.

17. The composition of claim 1, further comprising a short or medium chain fatty acid, or a mono-, di- or triglyceride of the short or medium chain fatty acid.

18. A composition for increasing ketone body level and modify metabolic function in a subject, the composition comprising:
    a mono- or di-ester of:
        S-beta-hydroxybutyrate; and
        1,3-butanediol; and
    at least one of:
        at least one ketone body salt selected from the group consisting of beta-hydroxybutyrate salts and acetoacetate salts, or
        at least one ketone body acid selected from the group consisting of beta-hydroxybutyric acid and acetoacetic acid.

19. A stacked composition for increasing ketone body level and modify metabolic function in a subject, the composition comprising:
    at least one ester selected from:
        an ester of S-beta-hydroxybutyrate; or
        an ester of S-1,3-butanediol and at least one ketone body; and
    at least one of:
        one or more ketone body salts selected from the group consisting of beta-hydroxybutyrate salts and acetoacetate salts, or
        one or more ketone body acids selected from the group consisting of beta-hydroxybutyric acid and acetoacetic acid.

20. The composition of claim 18 in a dosage form for oral consumption, wherein the dosage form is selected from the group consisting of powder, liquid, gel, suspension, tablet, capsule, food product, food additive, beverage, beverage additive, and food supplement and provides an oral dose of ketone bodies in a range of about 0.5 gram to about 50 grams.

21. A composition for increasing ketone body level and modifying metabolic function in a subject, the composition comprising:
    at least one ester or ester mixture selected from:
        an ester of S-beta-hydroxybutyrate or a non-racemic ester mixture enriched in S-beta-hydroxybutyrate relative to R-beta-hydroxybutyrate; or
        an ester of S-1,3-butanediol or a non-racemic ester mixture enriched in S-1,3-butanediol relative to R-1,3-butanediol; and
    at least one of:
        one or more ketone body salts selected from the group consisting of beta-hydroxybutyrate salts and acetoacetate salts, or
        one or more ketone body acids selected from the group consisting of beta-hydroxybutyric acid and acetoacetic acid.

* * * * *

UNITED STATES PATENT AND TRADEMARK OFFICE
CERTIFICATE OF CORRECTION

| | |
|---|---|
| PATENT NO. | : 11,202,769 B2 |
| APPLICATION NO. | : 17/130498 |
| DATED | : December 21, 2021 |
| INVENTOR(S) | : Gary Millet |

It is certified that error appears in the above-identified patent and that said Letters Patent is hereby corrected as shown below:

On the Title Page

Page 2, Column 2
Line 14, Item (56), Other Publications, change "Bastin et al., "Salt Slection and Optimisation Procedures for Pharmaceutical New Chemical Entities", American Chemical Society and The Royal Society of Chemistry, vol. 4, No. 5, 2000, pp. 427-435" to – Bastin et al., "Salt Selection and Optimisation Procedures for Pharmaceutical New Chemical Entities", American Chemical Society and The Royal Society of Chemistry, vol. 4, No. 5, 2000, pp. 427-435 –

Page 3, Column 2
Line 11, Item (56), Other Publications, change "Precision Xtra vs. NovaMax Plus: Ketone Meter Evaluation, Jimmy Moore's Livin' La Vida Low Garb Blog. Downloaded Apr. 1, 2015. http://livinlavidalowcarb.com/blog/precision-xtra-vs-novamax-plus-ketne-meter-evaluation/15918." to – Precision Xtra vs. NovaMax Plus: Ketone Meter Evaluation, Jimmy Moore's Livin' La Vida Low Carb Blog. Downloaded Apr. 1, 2015. http://livinlavidalowcarb.com/blog/precision-xtra-vs-novamax-plus-ketne-meter-evaluation/15918." –

In the Specification

Column 3
Line 14-15, change "have unpleasant taste" to – have an unpleasant taste –

Column 5
Line 24, change "compounds" to – compound –

Column 14
Line 15, change "delivery" to – deliver –

Column 17
Line 24, change "an" to – can –

Signed and Sealed this
Sixth Day of September, 2022

Katherine Kelly Vidal
*Director of the United States Patent and Trademark Office*